(12) United States Patent
Hu

(10) Patent No.: US 9,244,073 B2
(45) Date of Patent: Jan. 26, 2016

(54) ASSAYS FOR DETECTING ENZYMATIC ACTIVITY

(75) Inventor: Paul Q. Hu, Frederick, MD (US)

(73) Assignee: Wellstat Diagnostics, LLC, Gaithersburg, MD (US)

( * ) Notice: Subject to any disclaimer, the term of this patent is extended or adjusted under 35 U.S.C. 154(b) by 82 days.

(21) Appl. No.: 14/117,504

(22) PCT Filed: Feb. 24, 2012

(86) PCT No.: PCT/US2012/026497
§ 371 (c)(1),
(2), (4) Date: Jan. 27, 2014

(87) PCT Pub. No.: WO2012/154272
PCT Pub. Date: Nov. 15, 2012

(65) Prior Publication Data
US 2014/0141450 A1    May 22, 2014

Related U.S. Application Data

(60) Provisional application No. 61/446,751, filed on Feb. 25, 2011.

(51) Int. Cl.
G01N 33/53 (2006.01)
G01N 33/573 (2006.01)
C12Q 1/37 (2006.01)

(52) U.S. Cl.
CPC ............. *G01N 33/573* (2013.01); *C12Q 1/37* (2013.01); *G01N 2333/96444* (2013.01); *G01N 2333/96463* (2013.01)

(58) Field of Classification Search
None
See application file for complete search history.

(56) References Cited

U.S. PATENT DOCUMENTS

| | | | |
|---|---|---|---|
| 4,276,375 A | 6/1981 | Claeson et al. |
| 4,409,327 A | 10/1983 | Bartl et al. |
| 4,622,389 A | 11/1986 | Nagasawa et al. |
| 4,703,004 A | 10/1987 | Hopp et al. |
| 4,782,137 A | 11/1988 | Hopp et al. |
| 4,851,341 A | 7/1989 | Hopp et al. |
| 5,011,912 A | 4/1991 | Hopp et al. |
| 5,061,445 A | 10/1991 | Zoski et al. |
| 5,068,088 A | 11/1991 | Hall et al. |
| 5,093,268 A | 3/1992 | Leventis et al. |
| 5,147,806 A | 9/1992 | Kamin et al. |
| 5,171,662 A | 12/1992 | Sharma |
| 5,221,605 A | 6/1993 | Bard et al. |
| 5,238,808 A | 8/1993 | Bard et al. |
| 5,247,243 A | 9/1993 | Hall et al. |
| 5,296,191 A | 3/1994 | Hall et al. |
| 5,308,756 A | 5/1994 | van de Waart et al. |
| 5,310,687 A | 5/1994 | Bard et al. |
| 5,409,990 A | 4/1995 | Linnau et al. |
| 5,506,112 A | 4/1996 | Lang et al. |
| 5,627,038 A | 5/1997 | Hemker |
| 5,643,739 A | 7/1997 | Varadi et al. |
| 5,789,157 A | 8/1998 | Jensen et al. |
| 6,100,050 A | 8/2000 | Hemker et al. |
| 6,124,107 A | 9/2000 | Humes et al. |
| 6,140,062 A | 10/2000 | Wagenvoord et al. |
| 6,673,533 B1 | 1/2004 | Wohlstadter et al. |
| 6,875,741 B2 | 4/2005 | Pillutla et al. |
| 7,115,396 B2 | 10/2006 | Lipovsek et al. |
| 7,118,879 B2 | 10/2006 | Ladner et al. |
| 7,883,904 B2 | 2/2011 | Feldstein et al. |
| 8,409,878 B2 | 4/2013 | Feldstein et al. |
| 8,460,943 B2 | 6/2013 | Feldstein et al. |
| 2004/0018487 A1 | 1/2004 | Lu et al. |
| 2005/0014242 A1 | 1/2005 | Darrow et al. |
| 2007/0219354 A1 | 9/2007 | Hazuda et al. |
| 2008/0181885 A1 | 7/2008 | Raitano et al. |
| 2010/0120665 A1 | 5/2010 | Kaleko et al. |
| 2010/0203560 A1 | 8/2010 | Tamm et al. |

FOREIGN PATENT DOCUMENTS

| | | |
|---|---|---|
| EP | 0567636 B1 | 1/1997 |
| EP | 0656424 B1 | 2/2002 |
| EP | 1990057 A1 | 11/2008 |
| WO | 02/10439 A2 | 2/2002 |
| WO | WO 2003/027246 * | 4/2003 |
| WO | 03/084333 A1 | 10/2003 |
| WO | 2005/005657 A1 | 1/2005 |
| WO | 2009059972 A2 | 5/2009 |
| WO | 2011/014879 A2 | 2/2011 |

OTHER PUBLICATIONS

Agosto, et al., "Serum Caspase-3 p17 Fragment is Elevated in Patients with ST-Segment Elevation Myocardial Infarction: A Novel Observation", J Am Coll Cardiol, vol. 57:220-221 (2011).
Aniara, Ref. 221402, "Chromogenic Assay for Measuring Factor VIII:C in Plasma, or in Concentrates", retrieved from the internet: http://www.aniara.com/PROD/A221402.html; Jan. 11, 2010.
Aniara, Ref. A221010, "Two-stage Assay for the Measurement of Heparin, in Plasma and Purified Systems, Using an anti-Xa Chromogenic Method", retrieved from the internet: http://www.aniara.com/PROD/A221010-USP.html; Feb. 26, 2010.
Aniara, Ref. A221802, "Chromogenic Assay for Measuring Factor IX Activity in Plasma or Concentrates", retrieved from the internet: http://www.aniara.com/PROD/A221802.html, Jan. 13, 2010.
Babas, et al., "Indication of Participation of Caspase-2 and Caspase-5 in Mechanisms of Human Cervical Malignancy", International Journal of Gynecological Cancer, vol. 20(8):1381-1385 (2010).
Bantel, et al. "Detection of Apoptotic Caspase Activation in Sera from Patients with Chronic HCV Infection is Associated with Fibrotic Liver Injury" Hepatology, vol. 40(5):1078-1087 (2004).
Caulin, et al. "Caspase Cleavage of Keratin 18 and Reorganization of Intermediate Filaments during Epithelial Cell Apoptosis", Journal of Cell Biology, vol. 138:1379-1394 (1997).

(Continued)

*Primary Examiner* — Jennifer Graser

(57) ABSTRACT

The present invention relates to method of detecting activity of a sample. Some methods involve detecting a neo-binding-site created by the activity such as detecting an activity of a protease by detecting a neo-binding-site created by cleavage of a substrate by the protease.

32 Claims, 4 Drawing Sheets

(56) References Cited

OTHER PUBLICATIONS

Cummings, et al., "Biomarker Method Validation in Anticancer Drug Development", British Journal of Pharmacology, vol. 153:646-656 (2008).
Eich, et al., "Factor VIII Determination in Patient's Plasma and Concentrates: a Novel Test Equally Suited for Both Matrices", Blood Coagulation and Fibrinolysis, vol. 14:347-353 (2003).
Fischer, et al., "Many Cuts to Ruin: a Comprehensive Update of Caspase Substrates", Cell Death and Differentiation, vol. 10:76-100 (2003).
Forster, et al., "Electrogenerated Chemiluminescence", Annu Rev Anal Chem., vol. 2:359-385 (2009).
Girolami, et al., "Factor VIII Immunological Assay. An Evaluation of several Methods using whole Plasma", Blut, vol. 29(5):309-316 (1974).
Hacker, et al., "Increased Soluble Serum Markers Caspase-cleaved Cytokeratin-18, Histones, and ST2 Indicate Apoptotic Turnover and Chronic Immune Response in COPD", Journal of Clinical Laboratory Analysis, vol. 23(6):372-379 (2009).
Johnston, A., "The Relevance of Factor VIII (FVIII) Pharmacokinetics to TDM and Hemophilia a Treatment: is B Domain-Deleted FVIII Equivalent to Full-Length FVIII?", Ther Drug Monit, vol. 34(1):110-117 (2012).
Jones, et al., "Release of Proteolytic Activity Following Reduction in Therapeutic Human Serum Albumin Containing Products: Detection with a New Neoepitope Endopeptidase Immunoassay", Journal of Pharmaceutical and Biomedical Analysis, vol. 54:74-80 (2011).
Kim, et al., "Magnetic Bead-based Phage Anti-immunocomplex Assay (PHAIA) for the Detection of the Urinary Biomarker 3-Phenoxybenzoic Acid to Assess Human Exposure to Pyrethroid Insecticides", Anal. Biochem., vol. 386:45-52 (2009).
Kleinvield, et al., "Determination of Coagulation Factor VIII Activity by a Chromogenic Substrate Method on STA, an Automated Coagulation Analyzer", Scand J. Clin. Lab Invest., vol. 59:335-342 (1999).
Koo, et al., "Regulatory Mechanism of Matrix Metalloprotease-2 Enzymatic Activity by Factor Xa and Thrombin", Journal of Biological Chemistry, vol. 284(35):23375-23385 (2009).
Ku, et al., "Effect of Mutation and Phosphorylation of Type I Keratins on Their Caspase-mediated Degradation", J. Biol. Chem., vol. 276:26792-26798 (2001).
Leers, et al., "Immunocytochemical Detection and Mapping of a Cytokeratin 18 Neo-epitope Exposed During Early Apoptosis", Journal of Pathology., vol. 187:567-572 (1999).
MacFarlane, et al., "Active Caspases and Cleaved Cytokeratins Are Sequestered into Cytoplasmic Inclusions in TRAIL-induced Apoptosis", The Journal of Cell Biology, vol. 148(6):1239-1254 (2000).
Mathew, et al., "An Overview of Electrochemiluminescent (ECL) Technology in Laboratory Investigations", Kathmandu University Medical Journal, vol. 3:91-93 (2005).
Messai, et al., "Cytokeratin 18 Expression Pattern Correlates with Renal Cell Carcinoma Progression: Relationship with Snail", Int J Oncol., vol. 36(5):1145-1154 (2010).
Miesbach, et al., "Testing Factor VIII Activity by Using the Chromogenic Assay in Carriers of Hemophilia A", 34th Hemophilia Symposium Hamburg 2004, Springer Medizin Heidelberg Verlag 2004, pp. 179-182.
Mouawad, et al., "Serum Caspase-1 Levels in Metastatic Melanoma Patients: Relationship with Tumour Burden and Non-response to Biochemotherapy", Melanoma Res., vol. 12(4):343-348 (2002).
Palacios, et al., "Production of a Recombinant form of the Propeptide NH2-Terminal of the Precursor of Pulmonary Surfactant Protein B", Enzyme and Microbial Technology, vol. 40:85-92 (2006).
Papatheodoridis, et al., "Serum Apoptotic Caspase Activity as a Marker of Severity in HBeAg-Negative Chronic Hepatitis B Virus Infection", Gut, vol. 57:500-506 (2008) (Abstract).
Pietrak, et al., "Biochemical and Cell-based Assays for Characterization of BACE-1 inhibitors", Analytical Biochemistry, vol. 342:144-151 (2005).
Safi, Maa, "An Overview of Various Labeled Assays Used in Medical Laboratory Diagnosis", Saudi Medical Journal, vol. 31(4):359-368 (2010).
Sigma-Aldrich, Catalog No. F3040, "Monoclonal ANTI-FLAG® M1, Clone M1", retrieved from the internet: http://www.sigma-aldrich.com/cataloglproduct/sigma/f3040?lang=en&region=US, Aug. 13, 2010.
Soga, et al., "Molecular Cloning and Characterization of Prokineticin Receptors", Biochimica et Biophysica Acta, vol. 1579:173-179 (2002).
Tamm, et al., "Novel Immunoassay for Quantification of Brain Natriuretic Peptide and Its Precursor in Human Blood", Clinical Chemistry, vol. 54:1511-1518 (2008).
TechNotes, "Antibodies for New Type of BNP immunoassay— 'Single Epitope Sandwich' assay" (2010).
Voss, et al., "Anti-metatype Antibodies in Immunoassays", Mikrochim. Acta, vol. 126:193-202 (1997).
Wagenvoord, et al., "Development of a Simple Chromogenic Factor VIII Assay for Clinical Use", Haemostasis, vol. 19:196-204 (1989).
Wagenvoord, et al., "Development of a Sensitive and Rapid Chromogenic Factor IX Assay for Clinical Use", Haemostasis, vol. 20:276-288 (1990).
Wei, J. and LM Hendershot, "Characterization of the Nucleotide Binding Properties and ATPase Activity of Recombinant Hamster BiP Purified from Bacteria", The Journal of Biological Chemistry, vol. 270(44):26670-26676 (1995).
International Search Report for International Application No. PCT/US2012/026497 dated Oct. 4, 2012, and Written Opinion for International Application No. PCT/US2012/026497 dated Oct. 4, 2012.
Gehrie et al., "Test of the Month: The chromogenic antifactor Xa assay," Am. J. Hemotol. 87:194-196, 2012.
Harder et al., "Monitoring direct FXa-inhibitors and fondaparinux by Prothrombinase-induced Clotting Time (PiCT): Relation to FXa-activity and influence of assay modifications," Thrombosis Research. 123:396-403, 2008.
EPO Communication pursuant to Rule 164(1) EPC for Application No. EP 12781581.9, European Patent Office, dated Nov. 26, 2014.
European Search Report for Application No. EP 12781581.9, European Patent Office, dated Nov. 11, 2014.
Extended European Search Report for Application No. EP 12781581.9, European Patent Office, dated May 11, 2015.
Australian Patent Examination Report, dated Jan. 2015, for Australian Patent Application No. 2012254169.

* cited by examiner

E. Capture / Direct Detection

F. Capture / Indirect Detection

G. Capture/Competitive/Direct

H. Capture/Competitive/InDirect

SEQUENCE LISTING

<160> NUMBER OF SEQ ID NOS: 46

<210> SEQ ID NO 1
<211> LENGTH: 4
<212> TYPE: PRT
<213> ORGANISM: Artificial Sequence
<220> FEATURE:
<223> OTHER INFORMATION: FXa recognition site

<400> SEQUENCE: 1

Ile Glu Gly Arg
1

```
<210> SEQ ID NO 2
<211> LENGTH: 8
<212> TYPE: PRT
<213> ORGANISM: Artificial Sequence
<220> FEATURE:
<223> OTHER INFORMATION: includes binding site for anti-FLAG antibody

<400> SEQUENCE: 2

Asp Tyr Lys Asp Asp Asp Asp Lys
1               5

<210> SEQ ID NO 3
<211> LENGTH: 12
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 3

Ile Glu Gly Arg Asp Tyr Lys Asp Asp Asp Asp Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: includes binding site for anti-FLAG antibody

<400> SEQUENCE: 4

Asp Tyr Lys Asp Asp Asp Asp Lys Gly Ser
1               5                   10

<210> SEQ ID NO 5
<211> LENGTH: 14
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 5

Ile Glu Gly Arg Asp Tyr Lys Asp Asp Asp Lys Gly Ser
1               5                   10

<210> SEQ ID NO 6
<211> LENGTH: 6
<212> TYPE: PRT
<213> ORGANISM: Artificial Sequence
<220> FEATURE:
<223> OTHER INFORMATION: includes cleavage recognition site

<400> SEQUENCE: 6

Ile Glu Gly Arg Gly Ser
1               5

<210> SEQ ID NO 7
<211> LENGTH: 8
<212> TYPE: PRT
<213> ORGANISM: Artificial Sequence
<220> FEATURE:
<223> OTHER INFORMATION: comprises 6XHIS tag

<400> SEQUENCE: 7

Gly Ser His His His His His His
1               5
```

-continued

```
<210> SEQ ID NO 8
<211> LENGTH: 20
<212> TYPE: PRT
<213> ORGANISM: Artificial Sequence
<220> FEATURE:
<223> OTHER INFORMATION: comprises a FXa recognition site, a flag
      binding site and a 6XHIS tag

<400> SEQUENCE: 8

Ile Glu Gly Arg Asp Tyr Lys Asp Asp Asp Lys Gly Ser His His
1               5                   10                  15

His His His His
            20

<210> SEQ ID NO 9
<211> LENGTH: 6
<212> TYPE: PRT
<213> ORGANISM: Artificial Sequence
<220> FEATURE:
<223> OTHER INFORMATION: 6XHIS tag

<400> SEQUENCE: 9

His His His His His His
1               5

<210> SEQ ID NO 10
<211> LENGTH: 12
<212> TYPE: PRT
<213> ORGANISM: Artificial Sequence
<220> FEATURE:
<223> OTHER INFORMATION: includes a cleavage recognition site and flag
      binding site

<400> SEQUENCE: 10

Asp Ala Leu Asp Asp Tyr Lys Asp Asp Asp Asp Lys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: includes a cleavage recognition site and flag
      binding site

<400> SEQUENCE: 11

Val Glu Val Asp Asp Tyr Lys Asp Asp Asp Asp Lys
1               5                   10

<210> SEQ ID NO 12
<211> LENGTH: 12
<212> TYPE: PRT
<213> ORGANISM: Artificial Sequence
<220> FEATURE:
<223> OTHER INFORMATION: includes a cleavage recognition site and flag
      binding site

<400> SEQUENCE: 12

Val Glu Met Asp Asp Tyr Lys Asp Asp Asp Asp Lys
1               5                   10

<210> SEQ ID NO 13
<211> LENGTH: 4
<212> TYPE: PRT
<213> ORGANISM: Artificial Sequence
<220> FEATURE:
<223> OTHER INFORMATION: cleavage recognition site
```

```
<400> SEQUENCE: 13

Asp Glu Val Asp
1

<210> SEQ ID NO 14
<211> LENGTH: 4
<212> TYPE: PRT
<213> ORGANISM: Artificial Sequence
<220> FEATURE:
<223> OTHER INFORMATION: cleavage recognition site

<400> SEQUENCE: 14

Ile Glu Thr Asp
1

<210> SEQ ID NO 15
<211> LENGTH: 5
<212> TYPE: PRT
<213> ORGANISM: Artificial Sequence
<220> FEATURE:
<223> OTHER INFORMATION: cleavage recognition site

<400> SEQUENCE: 15

Val Asp Val Ala Asp
1               5

<210> SEQ ID NO 16
<211> LENGTH: 4
<212> TYPE: PRT
<213> ORGANISM: Artificial Sequence
<220> FEATURE:
<223> OTHER INFORMATION: cleavage recognition site

<400> SEQUENCE: 16

Val Glu Ile Asp
1

<210> SEQ ID NO 17
<211> LENGTH: 4
<212> TYPE: PRT
<213> ORGANISM: Artificial Sequence
<220> FEATURE:
<223> OTHER INFORMATION: cleavage recognition site

<400> SEQUENCE: 17

Tyr Val Ala Asp
1

<210> SEQ ID NO 18
<211> LENGTH: 4
<212> TYPE: PRT
<213> ORGANISM: Artificial Sequence
<220> FEATURE:
<223> OTHER INFORMATION: cleavage recognition site

<400> SEQUENCE: 18

Asp Ala Leu Asp
1

<210> SEQ ID NO 19
<211> LENGTH: 4
<212> TYPE: PRT
<213> ORGANISM: Artificial Sequence
<220> FEATURE:
<223> OTHER INFORMATION: cleavage recognition site
```

```
<400> SEQUENCE: 19

Val Glu Val Asp
1

<210> SEQ ID NO 20
<211> LENGTH: 4
<212> TYPE: PRT
<213> ORGANISM: Artificial Sequence
<220> FEATURE:
<223> OTHER INFORMATION: cleavage recognition site

<400> SEQUENCE: 20

Val Glu Met Asp
1

<210> SEQ ID NO 21
<211> LENGTH: 4
<212> TYPE: PRT
<213> ORGANISM: Artificial Sequence
<220> FEATURE:
<223> OTHER INFORMATION: cleavage recognition site

<400> SEQUENCE: 21

Ser Ser Thr Asp
1

<210> SEQ ID NO 22
<211> LENGTH: 4
<212> TYPE: PRT
<213> ORGANISM: Artificial Sequence
<220> FEATURE:
<223> OTHER INFORMATION: cleavage recognition site

<400> SEQUENCE: 22

Trp Glu His Asp
1

<210> SEQ ID NO 23
<211> LENGTH: 5
<212> TYPE: PRT
<213> ORGANISM: Artificial Sequence
<220> FEATURE:
<223> OTHER INFORMATION: cleavage recognition site

<400> SEQUENCE: 23

Val Glu Val Asp Asp
1               5

<210> SEQ ID NO 24
<211> LENGTH: 5
<212> TYPE: PRT
<213> ORGANISM: Artificial Sequence
<220> FEATURE:
<223> OTHER INFORMATION: cleavage recognition site

<400> SEQUENCE: 24

Val Glu Met Asp Asp
1               5

<210> SEQ ID NO 25
<211> LENGTH: 12
<212> TYPE: PRT
<213> ORGANISM: Artificial Sequence
<220> FEATURE:
<223> OTHER INFORMATION: includes cleavage recognition site and binding
      site for anti-FLAG antibody
```

```
<400> SEQUENCE: 25

Ser Ser Thr Asp Asp Tyr Lys Asp Asp Asp Asp Lys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 26

Asp Glu Val Asp Asp Tyr Lys Asp Asp Asp Asp Lys
1               5                   10

<210> SEQ ID NO 27
<211> LENGTH: 12
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 27

Ile Glu Thr Asp Asp Tyr Lys Asp Asp Asp Asp Lys
1               5                   10

<210> SEQ ID NO 28
<211> LENGTH: 13
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 28

Val Asp Val Ala Asp Asp Tyr Lys Asp Asp Asp Asp Lys
1               5                   10

<210> SEQ ID NO 29
<211> LENGTH: 12
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 29

Val Glu Ile Asp Asp Tyr Lys Asp Asp Asp Asp Lys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 30

Tyr Val Ala Asp Asp Tyr Lys Asp Asp Asp Asp Lys
1               5                   10
```

```
<210> SEQ ID NO 31
<211> LENGTH: 12
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 31

Trp Glu His Asp Asp Tyr Lys Asp Asp Asp Asp Lys
1               5                   10

<210> SEQ ID NO 32
<211> LENGTH: 4
<212> TYPE: PRT
<213> ORGANISM: Artificial Sequence
<220> FEATURE:
<223> OTHER INFORMATION: cleavage recognition site

<400> SEQUENCE: 32

Gly Pro Arg Pro
1

<210> SEQ ID NO 33
<211> LENGTH: 5
<212> TYPE: PRT
<213> ORGANISM: Artificial Sequence
<220> FEATURE:
<223> OTHER INFORMATION: cleavage recognition site

<400> SEQUENCE: 33

Asp Ile Pro Glu Asn
1               5

<210> SEQ ID NO 34
<211> LENGTH: 3
<212> TYPE: PRT
<213> ORGANISM: Artificial Sequence
<220> FEATURE:
<223> OTHER INFORMATION: cleavage recognition site

<400> SEQUENCE: 34

Ala Arg Gly
1

<210> SEQ ID NO 35
<211> LENGTH: 5
<212> TYPE: PRT
<213> ORGANISM: Artificial Sequence
<220> FEATURE:
<223> OTHER INFORMATION: cleavage recognition site

<400> SEQUENCE: 35

Ala Arg Gly Ser Val
1               5

<210> SEQ ID NO 36
<211> LENGTH: 7
<212> TYPE: PRT
<213> ORGANISM: Artificial Sequence
<220> FEATURE:
<223> OTHER INFORMATION: cleavage recognition site

<400> SEQUENCE: 36

Ala Arg Gly Ser Val Ile Leu
1               5
```

-continued

```
<210> SEQ ID NO 37
<211> LENGTH: 4
<212> TYPE: PRT
<213> ORGANISM: Artificial Sequence
<220> FEATURE:
<223> OTHER INFORMATION: cleavage recognition site

<400> SEQUENCE: 37

Phe Phe Gly Val
1

<210> SEQ ID NO 38
<211> LENGTH: 4
<212> TYPE: PRT
<213> ORGANISM: Artificial Sequence
<220> FEATURE:
<223> OTHER INFORMATION: cleavage recognition site

<400> SEQUENCE: 38

Thr Glu Gly Glu
1

<210> SEQ ID NO 39
<211> LENGTH: 4
<212> TYPE: PRT
<213> ORGANISM: Artificial Sequence
<220> FEATURE:
<223> OTHER INFORMATION: cleavage recognition site

<400> SEQUENCE: 39

Ile Asp Gly Arg
1

<210> SEQ ID NO 40
<211> LENGTH: 4
<212> TYPE: PRT
<213> ORGANISM: Artificial Sequence
<220> FEATURE:
<223> OTHER INFORMATION: cleavage recognition site

<400> SEQUENCE: 40

Ala Glu Gly Arg
1

<210> SEQ ID NO 41
<211> LENGTH: 12
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 41

Ile Asp Gly Arg Asp Tyr Lys Asp Asp Asp Asp Lys
1               5                   10

<210> SEQ ID NO 42
<211> LENGTH: 14
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 42

Ile Asp Gly Arg Asp Tyr Lys Asp Asp Asp Asp Lys Gly Ser
1               5                   10
```

```
<210> SEQ ID NO 43
<211> LENGTH: 20
<212> TYPE: PRT
<213> ORGANISM: Artificial Sequence
<220> FEATURE:
<223> OTHER INFORMATION: includes cleavage recognition site, binding
      site for anti-FLAG antibody and 6XHIS

<400> SEQUENCE: 43

Ile Asp Gly Arg Asp Tyr Lys Asp Asp Asp Lys Gly Ser His His
1               5                   10                  15

His His His His
            20

<210> SEQ ID NO 44
<211> LENGTH: 12
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 44

Ala Glu Gly Arg Asp Tyr Lys Asp Asp Asp Asp Lys
1               5                   10

<210> SEQ ID NO 45
<211> LENGTH: 14
<212> TYPE: PRT
<213> ORGANISM: Artificial Sequence
<220> FEATURE:
<223> OTHER INFORMATION: includes cleavage recognition site and binding
      site for anti-FLAG antibody

<400> SEQUENCE: 45

Ala Glu Gly Arg Asp Tyr Lys Asp Asp Asp Asp Lys Gly Ser
1               5                   10

<210> SEQ ID NO 46
<211> LENGTH: 20
<212> TYPE: PRT
<213> ORGANISM: Artificial Sequence
<220> FEATURE:
<223> OTHER INFORMATION: includes cleavage recognition site, binding
      site for anti-FLAG antibody and 6XHIS

<400> SEQUENCE: 46

Ala Glu Gly Arg Asp Tyr Lys Asp Asp Asp Asp Lys Gly Ser His His
1               5                   10                  15

His His His His
            20
```

ASSAYS FOR DETECTING ENZYMATIC ACTIVITY

This is a national stage application of International Application No. PCT/US2012/026497, filed internationally on Feb. 24, 2012, which claims priority to U.S. Provisional Patent Application No. 61/446,751, filed on Feb. 25, 2011, which is incorporated by reference herein in its entirety.

FIELD OF THE INVENTION

The present invention relates, in part, to methods of detecting a particular enzymatic activity in a sample. For example, the invention provides methods for detecting protease activity. The invention also provides substrates for measuring the activity of a sample.

BACKGROUND OF THE INVENTION

The detection of enzymatic activity is important in many aspects of biological research and in medical diagnosis and treatment. Abnormal enzymatic activity can be the cause of a disease state and/or a diagnostic and/or prognostic marker for a particular condition. There is a need in the art for improved assays for enzymatic activity such as protease activity.

For example, factor Xa (FXa), an activated serine endopeptidase, is a common blood factor involved in multiple coagulation pathways. Measurement of FXa activity is commonly employed in the determination of the activity of upstream coagulation factors including factor VIII (FVIII) and factor IX (FIX), as well as in the determination of the anticoagulant properties of pharmaceutical compounds such as heparin. Commercially available kits for these purposes typically contain chromogenic based substrates containing the amino acid sequence IEGR (SEQ ID NO:1), which is recognized and cleaved by FXa, resulting in the severing of the peptide bond between the arginine residue and the next amino acid or molecule toward the carboxy-terminus. For example, substrate S2222, Bz-Ile-Glu[γ-OR]-Gly-Arg-pNA.HCl (Para-Nitro-Aniline) [R=H (50%) and R=CH3 (50%)], a polypeptide with a pNA conjugated at its C-terminus, is found in several colorimetric kits for FVIII and FIX detection. FXa can digest this substrate and release pNA which, in its free form, produces a bright yellow color which can be quantitatively measured in an absorbance reader. Commercially available FVIII detection kits include BIOPHEN Factor IX (Ref. A221802. Aniara, Mason, Ohio 45040), BIOPHEN FVIII:C (Ref. A221406. Aniara), CHROMOGENIX COATEST® SP4 Factor VIII (Cat. K824094. DiaPharma Group, Inc. West Chester, Ohio 45069) and Rox Factor IX (Cat. 900020. DiaPharma Group, Inc.). An assay for detecting FVIII activity is described in U.S. Pat. No. 5,506,112.

Additionally, caspase enzymes are proteases involved in cellular inflammation and apoptotic cascades. The assessment of caspase enzymatic activity can be used to evaluate cell death pathways and new apoptosis-modulating agents. Failure of apoptosis has been implicated as one of the causes of many different diseases including tumor development and autoimmune diseases. Additionally, undesirable apoptosis can occur with ischemia or Alzheimer's disease.

Citation or discussion of a reference herein shall not be construed as an admission that such is prior art to the present invention.

SUMMARY OF THE INVENTION

The present invention relates, in part, to methods of detecting protease activity in a sample comprising combining in a solution at least the sample and a substrate under conditions compatible for the protease activity, wherein the substrate comprises an amino acid sequence, wherein the amino acid sequence comprises a cleavage site for the protease, wherein cleavage at the cleavage site generates a neo-binding-site and wherein the cleavage site is heterologous with respect to the neo-binding-site; and previously, subsequently or concurrently adding to the solution a first binding molecule, wherein the first binding molecule preferentially binds the neo-binding-site after cleavage of the substrate by the protease activity as compared to binding to the neo-binding-site in the uncleaved substrate; and detecting the binding of the first binding molecule to a fragment of the cleaved substrate.

In some embodiments, a neo-binding-site is located carboxy-terminal or amino-terminal to the cleavage site. In some embodiments, after cleavage of the substrate, the neo-binding-site is an amino-terminal amino acid sequence or a carboxy-terminal amino acid sequence. In some embodiments, an amino-terminal amino acid sequence comprises an amino acid sequence selected from the group consisting of DYKDDDDK (SEQ ID NO:2); DIPEN (SEQ ID NO:33); ARG (SEQ ID NO:34); ARGSV (SEQ ID NO:35); ARGSVIL (SEQ ID NO:36); and FFGV (SEQ ID NO:37). In some embodiments, a carboxy-terminal amino acid sequence comprises TEGE (SEQ ID NO:38).

In some embodiments, a binding molecule is an antibody that preferentially binds SEQ ID NO:2, e.g., a monoclonal antibody secreted by the murine hybridoma 4E11 (ATCC HB 9259). In some embodiments, the protease activity is FXa activity. In some embodiments, where protease activity is FXa activity, the cleavage site may comprise an amino acid sequence selected from the group consisting of IEGR (SEQ ID NO:1), IDGR (SEQ ID NO:39) and/or AEGR (SEQ ID NO:40).

In some embodiments, the protease activity is a caspase activity. In some embodiments, where the protease activity is caspase activity, the cleavage site may comprise an amino acid sequence selected from the group consisting of DEVD (SEQ ID NO:13), IETD (SEQ ID NO:14), VDVAD (SEQ ID NO:15), VEID (SEQ ID NO:16), YVAD (SEQ ID NO:17), DALD (SEQ ID NO:18), VEVD (SEQ ID NO:19), VEMD (SEQ ID NO:20), SSTD (SEQ ID NO:21) and WEHD (SEQ ID NO:22).

Some embodiments of the invention provide methods of detecting factor VIII activity in a sample comprising: combining in a solution at least the sample, a factor IXa, a thrombin, a factor X, and phospholipids under conditions compatible for the factor VIII activity and wherein FXa is produced if factor VIII activity is present in the sample; subsequently or concurrently adding a substrate to the solution, wherein the substrate comprises an amino acid sequence, wherein the amino acid sequence comprises a FXa cleavage site, wherein cleavage at the cleavage site generates a neo-binding-site and wherein the neo-binding-site is located on or bound to the uncleaved substrate at a site carboxy-terminal to the FXa cleavage site; adding a first binding molecule to the solution prior to, concurrently with or subsequent to adding the substrate to the solution, wherein the first binding molecule preferentially binds the neo-binding-site after cleavage of the substrate by the factor Xa as compared to binding of the neo-binding-site in the uncleaved substrate; and detecting the binding of the first binding molecule to a fragment of the cleaved substrate.

Some embodiments of the invention provide methods of detecting factor IX activity in a sample comprising: combining in a solution at least the sample, a factor XIa, a thrombin, a factor X, phospholipids and a factor VIII under conditions compatible for the factor IX activity and wherein FXa is produced if factor IX activity is present in the sample; subsequently or concurrently adding a substrate to the solution, wherein the substrate comprises an amino acid sequence, wherein the amino acid sequence comprises a FXa cleavage site, wherein cleavage at the cleavage site generates a neo-binding-site and wherein the neo-binding-site is located on or bound to the uncleaved substrate at a site carboxy-terminal to the FXa cleavage site; adding a first binding molecule to the solution prior to, concurrently with or subsequent to adding the substrate to the solution, wherein the first binding molecule preferentially binds the neo-binding-site, after cleavage of the substrate by the factor Xa, as compared to binding of the neo-binding-site in the uncleaved substrate; and detecting the binding of the first binding molecule to a fragment of the cleaved substrate.

Some embodiments of the invention provide methods of detecting factor VIII activity in a sample comprising: combining in a solution at least the sample, a thrombin, a factor IXa, a factor X, and phospholipids under conditions compatible for the factor VIII activity and wherein FXa is produced if factor VIII activity is present in the sample; subsequently or concurrently adding a substrate to the solution, wherein the substrate comprises an amino acid sequence, wherein the amino acid sequence comprises a FXa cleavage site, wherein cleavage at the cleavage site generates a neo-binding-site and wherein the neo-binding-site is located on or bound to the uncleaved substrate at a site carboxy-terminal to the FXa cleavage site; adding a first binding molecule to the solution prior to, concurrently with or subsequent to adding the substrate to the solution, wherein the first binding molecule preferentially binds the neo-binding-site after cleavage of the substrate by the factor Xa as compared to binding of the neo-binding-site in the uncleaved substrate; and detecting the binding of the first binding molecule to a fragment of the cleaved substrate.

Some embodiments of the invention provide methods of detecting factor IX activity in a sample comprising: combining in a solution at least the sample, a factor VIIIa, a factor X (FX) and phospholipids under conditions compatible for the factor IX activity and wherein FXa is produced if factor IX activity is present in the sample; subsequently or concurrently adding a substrate to the solution, wherein the substrate comprises an amino acid sequence, wherein the amino acid sequence comprises a FXa cleavage site, wherein cleavage at the cleavage site generates a neo-binding-site and wherein the neo-binding-site is located on or bound to the uncleaved substrate at a site carboxy-terminal to the FXa cleavage site; adding a first binding molecule to the solution prior to, concurrently with or subsequent to adding the substrate to the solution, wherein the first binding molecule preferentially binds the neo-binding-site after cleavage of the substrate by the factor Xa as compared to binding of the neo-binding-site in the uncleaved substrate; and detecting the binding of the first binding molecule to a fragment of the cleaved substrate.

Some embodiments of the invention provide methods of detecting heparin activity in a sample comprising: combining in a solution at least the sample, a FXa and a human antithrombin under conditions compatible for the heparin activity; subsequently or concurrently adding a substrate to the solution, wherein the substrate comprises an amino acid sequence, wherein the amino acid sequence comprises a FXa cleavage site, wherein cleavage at the cleavage site generates a neo-binding-site and wherein the neo-binding-site is located on or bound to the uncleaved substrate at a site carboxy-terminal to the FXa cleavage site; adding a first binding molecule to the solution prior to, concurrently with or subsequent to adding the substrate to the solution, wherein the first binding molecule preferentially binds the neo-binding-site after cleavage of the substrate by the factor Xa as compared to binding of the neo-binding-site in the uncleaved substrate; and detecting the binding of the first binding molecule to a fragment of the cleaved substrate.

Some embodiments of the invention utilize a thrombin selected from the group consisting of human α-thrombin, bovine α-thrombin and mouse thrombin.

In some embodiments, a substrate comprises an amino acid sequence selected from the group consisting of SEQ ID NO:2, 3, 4, 5, 8, 10, 11, 12, 25, 26, 27, 28, 29, 30, 31, 41, 42, 43, 44, 45, and 46. In some embodiments, a substrate comprises amino acid sequence SEQ ID NO:2 or SEQ ID NO:4 immediately carboxy-terminal to a cleavage site, such as a FXa cleavage site.

Some assays of the invention utilize GPRP-NH$_2$ (SEQ ID NO:32), for example, to block the formation of fibrin network which, in some cases, can interfere with particular assay types or formats, such as those using beads.

Some assays of the invention utilize calcium. Some embodiments of the invention utilize a thrombin inhibitor such as, but not limited to, hirudin, bivalirudin, lepirudin, desirudin, argatroban, melagatran, dabigatran, I-2581, ximelagatran, antithrombin, human antithrombin and heparin.

Binding molecules that can be used in the invention include, but are not limited to, an antibody, an aptamer, a ligand and a receptor. In some embodiments, a binding molecule (e.g., a neo-binding-site binding molecule) comprises at least one detection label. Some embodiments of the invention utilize a second binding molecule, wherein the second binding molecule comprises (i) at least one detection label and (ii) binds the first binding molecule (e.g., a neo-binding-site binding molecule).

In some embodiments, a neo-binding-site comprises or consists of an amino acid sequence. In some embodiments, a neo-binding-site comprises or consists of an amino acid sequence selected from the group consisting of DYKD-DDDK (SEQ ID NO:2), DIPEN (SEQ ID NO:33), ARG (SEQ ID NO:34), ARGSV (SEQ ID NO:35), ARGSVIL (SEQ ID NO:36) and FFGV (SEQ ID NO:37). In some embodiments, a neo-binding-site comprises or consists of amino acid sequence TEGE (SEQ ID NO:38)

In some embodiments, a substrate is bound to a surface and the surface binds the substrate at a site carboxy-terminal of a cleavage site, such as a FXa cleavage site.

Some embodiments of the invention utilize a competitive molecule comprising a second binding site that competes with binding of a first binding molecule to a neo-binding-site in the cleaved substrate. In some embodiments, a competitive molecule is bound or attached to a surface. In some embodiments, the competitive molecule is covalently bound to a surface. Some embodiments utilize a second binding molecule that binds the competitive molecule at a different site than the first binding molecule and in some cases the second binding molecule can be bound or attached to a surface.

In some embodiments, a solution containing a substrate further comprises a second binding molecule, wherein the second binding molecule binds the substrate at a site carboxy-terminal to a cleavage site. In some embodiments, this second binding molecule is bound to a surface.

In some embodiments of the invention, a neo-binding-site binding molecule is bound to a surface.

In some embodiments of the invention, a substrate comprises at least one detection label and the at least one detection label is bound to the substrate at a site located carboxy-terminal to a cleavage site and a neo-binding-site in the cleaved substrate can be bound by a neo-binding-site binding molecule.

In some embodiments, a substrate containing solution comprises a second binding molecule and the second binding molecule (i) comprises at least one detection label and (ii) binds the substrate at a site carboxy-terminal of a cleavage site and wherein a neo-binding-site in the cleaved substrate can be bound by the first binding molecule.

In some embodiments of the invention, a surface is a bead, such as a paramagnetic bead.

Some embodiments provide methods to quantify the amount of factor Xa activity in the sample.

The invention includes compositions comprising: (a) a substrate, wherein the substrate comprises an amino acid sequence, wherein the amino acid sequence comprises a cleavage site for a protease, wherein cleavage at the cleavage site generates a neo-binding-site and wherein the cleavage site is heterologous with respect to the neo-binding-site; and optionally (b) a first binding molecule, wherein the first binding molecule preferentially binds the neo-binding-site after cleavage of the substrate by the protease as compared to binding to the neo-binding-site in the uncleaved substrate. In some embodiments, a neo-binding-site is located or bound to the substrate at a site carboxy-terminal to a cleavage site. In some embodiments, a cleavage site comprises an amino acid sequence selected from the group consisting of IEGR (SEQ ID NO:1), IDGR (SEQ ID NO:39), AEGR (SEQ ID NO:40), DEVD (SEQ ID NO:13), IETD (SEQ ID NO:14), VDVAD (SEQ ID NO:15), VEID (SEQ ID NO:16), YVAD (SEQ ID NO:17), DALD (SEQ ID NO:18), VEVD (SEQ ID NO:19), VEMD (SEQ ID NO:20), SSTD (SEQ ID NO:21) and WEHD (SEQ ID NO:22).

The invention also includes compositions comprising: (a) a substrate, wherein the substrate comprises an amino acid sequence, wherein the amino acid sequence comprises a FXa cleavage site, wherein cleavage at the cleavage site generates a neo-binding-site and wherein the neo-binding-site is located or bound to the uncleaved substrate at a site carboxy-terminal to the FXa cleavage site; and optionally (b) a first binding molecule, wherein the first binding molecule preferentially binds the neo-binding-site after cleavage of the substrate by a FXa as compared to binding to the neo-binding-site in the uncleaved substrate. In some embodiments, a FXa cleavage site is heterologous with regard to the neo-binding-site. In some embodiments, this composition further comprises (i) factor IXa, an alpha-thrombin, a FX and phospholipids; (ii) factor VIII, an alpha-thrombin, a FX and phospholipids; or (iii) factor VIIIa, a FX and phospholipids. Some compositions of the invention comprise GPRP-NH2 (SEQ ID NO:32) and/or calcium.

The invention also provides peptides or proteins comprising the amino acid sequence IEGRDYKDDDDK (SEQ ID NO:3), IDGRDYKDDDDK (SEQ ID NO:41), AEGRDYKDDDDK (SEQ ID NO:44), IEGRDYKDDDDKGS (SEQ ID NO:5), IEGRDYKDDDDKGSHHHHHH (SEQ ID NO:8), IDGRDYKDDDDKGS (SEQ ID NO:42), IDGRDYKDDDDKGSHHHHHH (SEQ ID NO:43), AEGRDYKDDDDKGS (SEQ ID NO:45) or AEGRDYKDDDDKGSHHHHHH (SEQ ID NO:46). Additionally, the invention provides peptides or proteins wherein the amino acid sequence consists of IEGRDYKDDDDK (SEQ ID NO:3), IEGRDYKDDDDKGS (SEQ ID NO:5), IEGRDYKDDDDKGSHHHHHH (SEQ ID NO:8), IDGRDYKDDDDK (SEQ ID NO:41), IDGRDYKDDDDKGS (SEQ ID NO:42), IDGRDYKDDDDKGSHHHHHH (SEQ ID NO:43), AEGRDYKDDDDK (SEQ ID NO:44), AEGRDYKDDDDKGS (SEQ ID NO:45), and AEGRDYKDDDDKGSHHHHHH (SEQ ID NO:46). A peptide or protein of the invention may further comprise a detection label bound to the peptide or protein. In some embodiments, a detection label is bound or attached to a peptide or protein at a site carboxy-terminal to an amino acid sequence selected from the group consisting of IEGR (SEQ ID NO:1), IDGR (SEQ ID NO:39), AEGR (SEQ ID NO:40), DEVD (SEQ ID NO:13), IETD (SEQ ID NO:14), VDVAD (SEQ ID NO:15), VEID (SEQ ID NO:16), YVAD (SEQ ID NO:17), DALD (SEQ ID NO:18), VEVD (SEQ ID NO:19), VEMD (SEQ ID NO:20), SSTD (SEQ ID NO:21) and WEHD (SEQ ID NO:22). In some embodiments, a detection label is bound or attached to a peptide or protein at a site amino-terminal to a DYKDDDDK (SEQ ID NO:2) amino acid sequence.

It is contemplated that any method or composition described herein can be implemented with respect to any other method or composition described herein. The use of the word "a" or "an" when used in conjunction with the term "comprising" in the claims and/or the specification may mean "one," but it is also consistent with the meaning of "one or more," "at least one," and "one or more than one." The use of the term/phrase "and/or" when used with a list means one or more of the listed items may be utilized, e.g., it is not limited to one or all of the elements.

This summary of the invention does not necessarily describe all features or necessary features of the invention. The invention may also reside in a sub-combination of the described features.

BRIEF DESCRIPTION OF THE FIGURES

For the purpose of illustrating the invention, there are depicted in the drawings certain embodiments of the invention. However, the invention is not limited to the precise arrangements and instrumentalities of embodiments depicted in the drawings.

FIGS. 1A-H are described in more detail below. Briefly, FIG. 1A depicts a format with a substrate attached/bound to a surface and detection of the epitope or neo-binding-site is by detecting binding of a labeled binding molecule. FIG. 1B depicts a competitive format where the neo-binding-site of the cleaved substrate competes with a surface bound/attached molecule for binding of the labeled binding. FIG. 1C depicts a non-competitive assay that utilizes a sandwich format with a labeled binding molecule that preferentially binds a neo-binding-site of a cleaved substrate and the cleaved substrate is also bound by a capture binding molecule. FIG. 1D depicts a competitive assay that utilizes a sandwich format with a labeled binding molecule that preferentially binds a neo-binding-site. The format depicted in FIG. 1E utilizes a labeled substrate where the cleaved labeled substrate is preferentially bound to a surface, e.g., using a binding molecule that preferentially binds a neo-binding-site in the cleaved substrate. The format depicted in FIG. 1F differs from FIG. 1C in that the binding molecule on the surface binds a neo-binding-site of a cleaved substrate, whereas in FIG. 1C the labeled binding molecule binds the neo-binding-site. FIG. 1G depicts a competitive assay format where the cleaved substrate competes with a labeled molecule (sometimes referred to as a probe) for binding to a surface, wherein the surface comprises a binding molecule that preferentially binds the cleaved substrate. FIG. 1H depicts a competitive sandwich assay format, which differs from FIG. 1D in that the binding molecule on the surface binds the neo-binding-site, whereas in FIG. 1D the labeled binding molecule binds the neo-binding-site.

FIGS. 2A and 2B differ from FIGS. 2C and 2D, respectively, in that the substrates are bound to the surface by a binding molecule. In the assay formats of FIGS. 2A-D, the label is released from the bound substrate when cleaved by the protease.

BRIEF DESCRIPTION OF THE SEQUENCES

Figure 1:
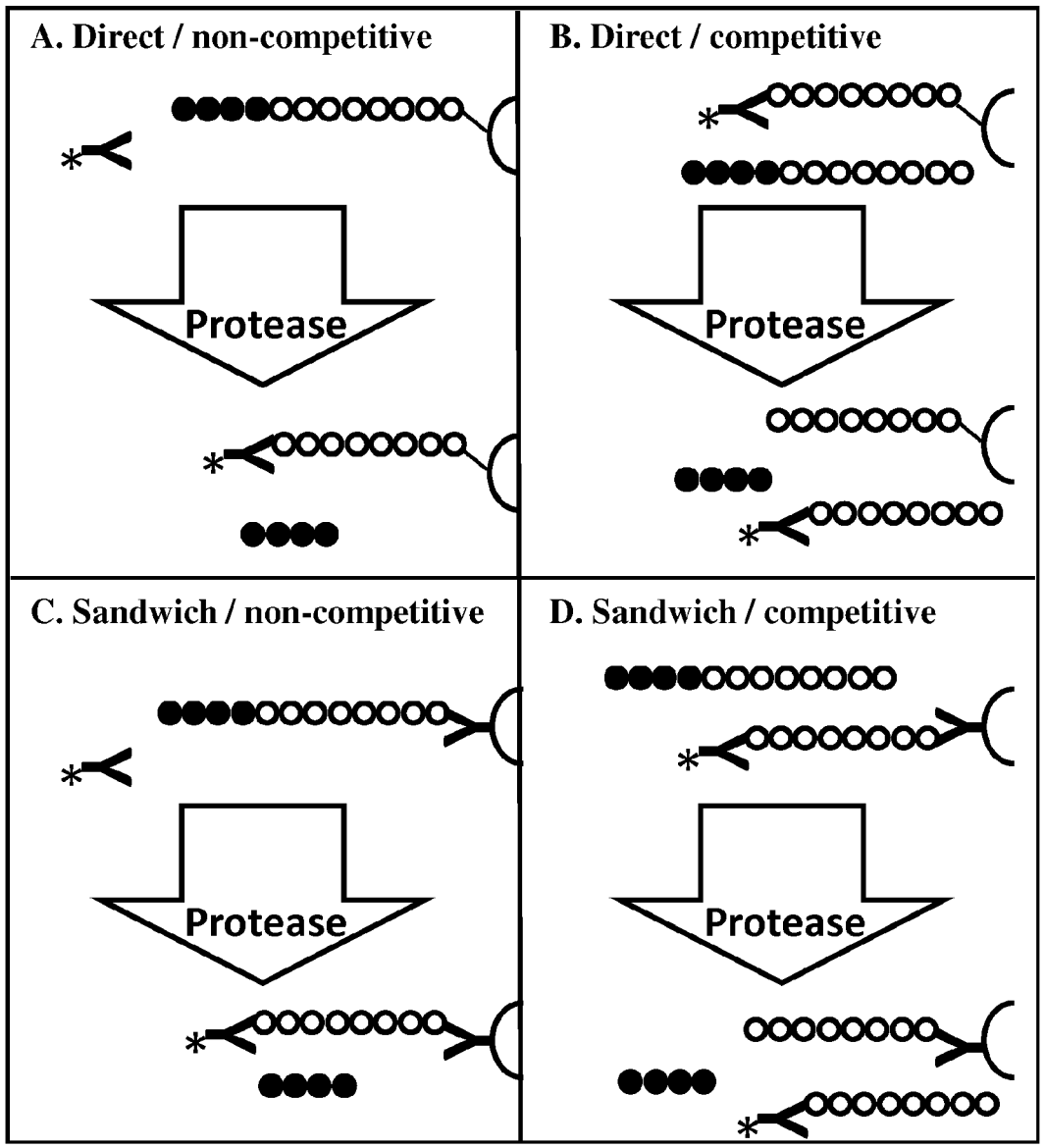
FIG. 1 depicts various exemplary assay formats that may be utilized in accordance with the invention. These assay formats are depicted in the context of the detection of protease activity only as non-limiting examples of assay formats. Some of these formats can utilize an epitope, neoepitope and/or neo-binding-site; a cleavage site (e.g., IEGR (SEQ ID NO:1)); a binding molecule that binds the epitope, neoepitope and/or neo-binding-site; a binding molecule that is utilized to immobilize or capture the substrate; a detectable label (*); or combinations thereof. The substrate comprises a protease cleavage site and a binding site (e.g., an epitope, neoepitope or neo-binding-site). These formats may be utilized to detect activity of various proteases by using different recognition sites (e.g., cleavage sites) that correspond to the activity to be detected and/or using different binding sites.

SEQ ID NO:1 is the amino acid sequence IEGR (SEQ ID NO:1).
SEQ ID NO:2 is the amino acid sequence DYKDDDDK (SEQ ID NO:2).
SEQ ID NO:3 is the amino acid sequence IEGRDYKDDDDK (SEQ ID NO:3).
SEQ ID NO:4 is the amino acid sequence DYKDDDDKGS (SEQ ID NO:4).
SEQ ID NO:5 is the amino acid sequence IEGRDYKDDDDKGS (SEQ ID NO:5).
SEQ ID NO:6 is the amino acid sequence IEGRGS (SEQ ID NO:6).
SEQ ID NO:7 is the amino acid sequence GSHHHHHH (SEQ ID NO:7).
SEQ ID NO:8 is the amino acid sequence IEGRDYKDDDDKGSHHHHHH (SEQ ID NO:8).
SEQ ID NO:9 is the amino acid sequence HHHHHH (SEQ ID NO:9).
SEQ ID NO:10 is the amino acid sequence DALDDYKDDDDK (SEQ ID NO:10).
SEQ ID NO:11 is the amino acid sequence VEVDDYKDDDDK (SEQ ID NO:11).
SEQ ID NO:12 is the amino acid sequence VEMDDYKDDDDK (SEQ ID NO:12).
SEQ ID NO:13 is the amino acid sequence DEVD (SEQ ID NO:13).
SEQ ID NO:14 is the amino acid sequence IETD (SEQ ID NO:14).
SEQ ID NO:15 is the amino acid sequence VDVAD (SEQ ID NO:15).
SEQ ID NO:16 is the amino acid sequence VEID (SEQ ID NO:16).
SEQ ID NO:17 is the amino acid sequence YVAD (SEQ ID NO:17).
SEQ ID NO:18 is the amino acid sequence DALD (SEQ ID NO:18).
SEQ ID NO:19 is the amino acid sequence VEVD (SEQ ID NO:19).
SEQ ID NO:20 is the amino acid sequence VEMD (SEQ ID NO:20).
SEQ ID NO:21 is the amino acid sequence SSTD (SEQ ID NO:21).
SEQ ID NO:22 is the amino acid sequence WEHD (SEQ ID NO:22).
SEQ ID NO:23 is the amino acid sequence VEVDD (SEQ ID NO:23).
SEQ ID NO:24 is the amino acid sequence VEMDD (SEQ ID NO:24).
SEQ ID NO:25 is the amino acid sequence SSTDDYKDDDDK (SEQ ID NO:25).
SEQ ID NO:26 is the amino acid sequence DEVDDYKDDDDK (SEQ ID NO:26).
SEQ ID NO:27 is the amino acid sequence IETDDYKDDDDK (SEQ ID NO:27).
SEQ ID NO:28 is the amino acid sequence VDVADDYKDDDDK (SEQ ID NO:28).
SEQ ID NO:29 is the amino acid sequence VEIDDYKDDDDK (SEQ ID NO:29).
SEQ ID NO:30 is the amino acid sequence YVADDYKDDDDK (SEQ ID NO:30).
SEQ ID NO:31 is the amino acid sequence WEHDDYKDDDDK (SEQ ID NO:31).
SEQ ID NO:32 is the amino acid sequence GPRP (SEQ ID NO:32).
SEQ ID NO:33 is the amino acid sequence DIPEN (SEQ ID NO:33).
SEQ ID NO:34 is the amino acid sequence ARG (SEQ ID NO:34).
SEQ ID NO:35 is the amino acid sequence ARGSV (SEQ ID NO:35).
SEQ ID NO:36 is the amino acid sequence ARGSVIL (SEQ ID NO:36).
SEQ ID NO:37 is the amino acid sequence FFGV (SEQ ID NO:37).
SEQ ID NO:38 is the amino acid sequence TEGE (SEQ ID NO:38)
SEQ ID NO:39 is the amino acid sequence IDGR (SEQ ID NO:39).
SEQ ID NO:40 is the amino acid sequence AEGR (SEQ ID NO:40).
SEQ ID NO:41 is the amino acid sequence IDGRDYKDDDDK (SEQ ID NO:41).
SEQ ID NO:42 is the amino acid sequence IDGRDYKDDDDKGS (SEQ ID NO:42).
SEQ ID NO:43 is the amino acid sequence IDGRDYKDDDDKGSHHHHHH (SEQ ID NO:43).
SEQ ID NO:44 is the amino acid sequence AEGRDYKDDDDK (SEQ ID NO:44).
SEQ ID NO:45 is the amino acid sequence AEGRDYKDDDDKGS (SEQ ID NO:45).
SEQ ID NO:46 is the amino acid sequence AEGRDYKDDDDKGSHHHHHH (SEQ ID NO:46).

DETAILED DESCRIPTION

As used herein the transitional term "comprising" is open-ended. A claim utilizing this term can contain elements in addition to those recited in such claim. Thus, for example, the claims can read on methods that also include other steps not specifically recited therein, as long as the recited elements or their equivalent are present.

A "neoepitope" or "neo-binding-site" is an epitope or binding site in a molecule (e.g., a protein or peptide) where after cleavage, protease cleavage or degradation of the molecule, the epitope or binding site can be preferentially bound by a binding molecule as compared to binding of the binding molecule to the epitope or binding site in the uncleaved molecule. For example, cleavage of the molecule enhances binding to the neoepitope or neo-binding-site by the binding molecule. A neoepitope is a neo-binding-site. In some embodiments, cleavage of the molecule enhances the affinity of the binding to the neoepitope or neo-binding-site by the binding molecule. In some embodiments, a binding molecule does not bind the neoepitope or neo-binding-site until after cleavage, protease cleavage or degradation of the molecule. A neoepitope or neo-binding-site can be present in an uncleaved molecule and, after cleavage, it typically becomes exposed, more accessible for binding and/or modified so that a binding molecule binds it more efficiently and/or with higher affinity. In some embodiments, a neoepitope or neo-binding-site is a linear amino acid sequence. In some embodiments, a neoepitope or neo-binding-site is not a linear amino acid sequence. In some embodiments, a conformational change in the molecule due to an enzymatic activity (e.g., cleavage and/or degradation of the molecule) forms, exposes and/or makes more accessible for binding a neoepitope or neo-binding-site.

A "heterologous neo-binding-site" is a neo-binding-site that is heterologous to the cleavage site in a molecule. A heterologous neo-binding-site would not be found in nature in the same molecule as the cleavage site.

Neoepitope antibodies or neo-binding-site binding molecules specifically or preferentially bind a neoepitope or neo-binding-site. A neoepitope antibody is a type of neo-binding-site binding molecule. The binding is specific or preferential when compared to binding the same site (e.g., sequence of amino acids) present in the intact, uncleaved or non-degraded molecule. In some instances, a neoepitope antibody or neo-binding-site binding molecule binds a newly created N or C terminus of a protein.

An "anti-neo-binding-site binding molecule" is a binding molecule capable of binding the particular neo-binding-site.

An "exposed neo-binding-site" refers to a binding site that can bind with an anti-neo-binding-site binding molecule. In some embodiments, an exposed neo-binding-site is used in a competitive assay format of the invention. In some embodiments, an exposed neo-binding-site is capable of competing with a neo-binding-site in a cleaved substrate for binding of an anti-neo-binding-site binding molecule.

Some embodiments of the invention are based on detecting the protease activity of a sample using a substrate that comprises a cleavage site for the protease and wherein cleavage of the substrate allows a binding molecule to preferentially bind a neo-binding-site (e.g., a neoepitope) as compared to the neo-binding-site in the uncleaved substrate. In some embodiments, the neo-binding-site is heterologous to the cleavage site. For example, when a cleavage site is typically found in nature as part of an amino acid sequence that does not comprise the neo-binding-site, then the cleavage site and the neo-binding-site are heterologous. They are also considered heterologous where the neo-binding-site is typically found in nature as part of an amino acid sequence that does not comprise the cleavage site. Additionally, they would also be considered heterologous if neither the neo-binding-site nor the cleavage site is found in nature.

The cleavage site can be a native or a non-native cleavage site such as an optimized cleavage site. A "native cleavage site" is one that occurs in nature and can be cleaved by the particular protease activity of interest. A "non-native cleavage site" is one not known to occur in nature, but can be cleaved by the particular protease activity of interest. For example, in some instances a native cleavage site may not be an optimal cleavage site for the protease activity. In some embodiments, a non-native cleavage site can be a cleavage site that is cleaved by a protease more efficiently in an assay than a native cleavage site. Therefore some aspects of the invention contemplate use a non-native cleavage site, such as one obtained through screening various mutations (e.g., of a native cleavage site) or even a library of possible mutant cleavage sites. For example, see Patent Publication No. 20070219354 (Hazuda et al.) and Pietrak et al. (Analytical Biochemistry, 2005, 342:144-151) which describe optimizing a peptide cleavage site for more efficient cleavage by the corresponding protease, BACE-1 (β-Secretase). Using substrates that can be cleaved more efficiently will typically result in a higher sensitivity or lower detection limit for the particular assay. Although for many applications high sensitivity or low detection limits may not be important or required, so a cleavage site could be a non-native cleavage site that is cleaved less efficiently in an assay than a native cleavage site. In some embodiments, a cleavage site for FXa is utilized where the FXa cleavage site is not a native cleavage site.

Some embodiments of the invention contemplate detection assay formats that utilize detection of a neo-binding-site to correlate with the protease activity of a sample. The protease activity can be from, but not limited to, a serine protease, threonine protease, a cysteine protease, an aspartate protease, a metalloprotease or a glutamic acid protease. In some embodiments, detected protease activity is from an endopeptidase.

The invention provides, inter alia, methods for detecting FIX, FXa, heparin and FVIII activity. FVIII activity can be from, but is not limited to, activity from naturally purified FVIII, recombinant FVIII, B-domain-deleted recombinant factor VIII (e.g., Xyntha, Wyeth) and long-lasting recombinant factor VIII Fc fusion protein (rFVIIIFc). Some methods and assays of the invention utilize the detection of resulting factor Xa activity as a correlation of the FVIII or FIX activity in a sample. Some embodiments provide assays and methods for quantifying the amount of FVIII or FIX in a sample by quantifying the amount of resulting FXa activity from a sample. Some embodiments provide assays and methods for quantifying the amount of heparin in a sample by quantifying the amount of resulting FXa activity from a sample. In some embodiments, the amount of heparin in a sample will be inversely proportional to the amount of detected FXa activity.

The invention also provides methods for detecting thrombin activity. In the blood coagulation pathway, thrombin acts to convert factor XI to XIa, VIII to VIIIa, V to Va, and fibrinogen to fibrin. Therefore, thrombin activity can be detected using assays described herein for detecting factor Xa, VIIIa or Va.

The invention also provides methods for detecting caspase activity.

Assays and methods of the invention can be qualitative and/or quantitative.

Assays of the invention can be utilized to detect activity in a variety of samples including samples prepared from tissue or body fluids from an animal or human, blood, plasma, serum, saliva, urine, cell culture supernatants, cell lysates, cleared cell lysates, cell extracts, tissue extracts, sputum, semen, mucus, milk, synovial fluid, pleural fluid, edema fluid, spinal fluid, and fractions thereof.

Assay Formats

Some assay formats of the invention are based on the detection of a neo-binding-site from a cleaved substrate. In some embodiments, detection of a neo-binding-site is by detecting binding of a binding molecule that specifically or preferentially binds the neo-binding-site. In some embodiments, a neo-binding-site is an epitope. In some embodiments, a neo-binding-site is N-terminal or C-terminal. In some embodiments, a binding molecule is an anti-neoepitope antibody.

The invention encompasses many different formats in which an assay can be designed to detect the neo-binding-site. These formats include, but are not limited to, immunoassays, competitive formats, directly labeled neoepitope-substrate formats and single epitope sandwich formats.

The following is meant to show examples of some formats encompassed by the invention, but is not meant to limit the invention to the specific formats as described herein.

FIG. 1 depicts non-limiting examples of various assay formats that can be used in conjunction with the invention. FIG. 1 depicts various formats in terms of protease activity, a substrate comprising a cleavage site (e.g., IEGR (SEQ ID NO:1)), wherein cleavage at the cleavage site generates a neo-binding-site and a binding molecule (e.g., an antibody) that preferentially binds the neo-binding-site in the cleaved substrate as compared to binding in the uncleaved substrate.

FIG. 1A depicts a format where a substrate (e.g., a FXa substrate) is bound by or attached to a surface (e.g., a bead or plate). The substrate comprises a cleavage site, wherein cleavage at the cleavage site generates/exposes a neo-binding-site. The surface is bound to the substrate. A sample is combined/reacted with the substrate under proper conditions and with any reagents/compounds necessary for detecting the protease activity of the sample. A labeled binding molecule is added to the sample either before, concurrently or after the sample and substrate are combined. The labeled binding molecule preferentially binds the neo-binding-site in the cleaved substrate as compared to uncleaved. If the sample contains the particular protease activity, the substrate is cleaved which allows the labeled binding molecule to bind the neo-binding-site. After a sufficient amount of time to allow binding, a majority of the unbound components can be optionally removed or washed away and any remaining labeled binding molecule is detected. A higher amount of signal from the label correlates with a higher amount of protease activity in the sample.

The format depicted in FIG. 1B is a competitive format where the uncleaved substrate is not attached to a surface, but a molecule comprising an exposed neo-binding-site is attached to or bound to a surface. Therefore, the labeled anti-neo-binding-site binding molecule binds to the exposed neo-binding-site that is attached to or bound to the surface. If the sample contains protease activity, the unbound substrate is cleaved. This allows the neo-binding-site of the cleaved unbound substrate to compete with the exposed neo-binding-site (attached to the surface) for binding of the anti-neo-binding-site binding molecule. After a sufficient amount of time to allow for binding, a majority of the unbound components can optionally be removed or washed away and any remaining labeled binding molecule is detected. In this format, a lower amount of signal from the label correlates with a higher amount of protease activity.

The format depicted in FIG. 1C differs from FIG. 1A in that a surface comprises a capture binding molecule that binds (captures) a substrate (e.g., cleaved; or cleaved and uncleaved) and wherein the binding by the capture binding molecule does not significantly interfere with binding of the neo-binding-site by the anti-neo-binding-site binding molecule after cleavage of the substrate. The anti-neo-binding-site binding molecule preferentially binds the anti-neo-binding-site after cleavage of the substrate. A higher amount of signal from the label correlates with a higher amount of protease activity.

The format depicted in FIG. 1D differs from FIG. 1B in that the surface comprises a binding molecule that can bind the other molecule (probe) comprising the already exposed neo-binding-site. Therefore in the presence of the particular protease, the substrate is cleaved and competes with the other molecule (probe) comprising the exposed neo-binding-site for binding of the labeled anti-neo-binding-site binding molecule. A lower amount of signal from the label correlates with a higher amount of protease activity.

Figure 1E:
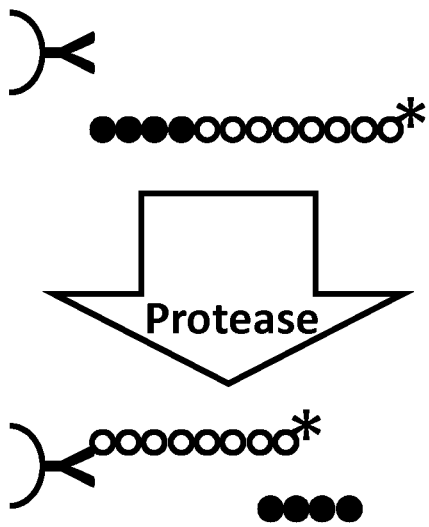

The format depicted in FIG. 1E comprises a surface comprising a (capture) binding molecule that preferentially binds the neo-binding-site of the cleaved substrate as compared to the uncleaved substrate. In this format the substrate is labeled so that after cleavage of the substrate, the fragment comprising the neo-binding-site also comprises the label. After a sufficient amount of time to allow for binding, the unbound components can optionally be removed or washed away and any remaining labeled binding molecule is detected. A higher amount of signal from the label correlates with a higher amount of protease activity.

Figure 1F:
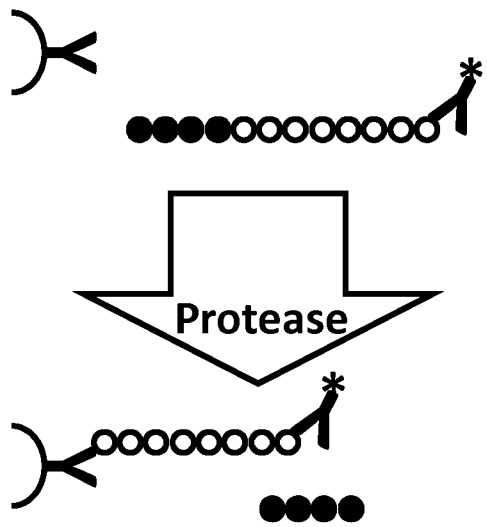

The format depicted in FIG. 1F differs from FIG. 1E in that the substrate is unlabeled and the format additionally comprises a second binding molecule that is labeled and the labeled second binding molecule binds the cleaved substrate fragment containing the neo-binding-site. It is preferable that the labeled second binding molecule's binding of the fragment does not interfere with binding of the neo-binding-site to the capture binding molecule. The invention also contemplates a format similar to that depicted in FIG. 1F except that a substrate is directly labeled at a site(s) in the substrate so that the cleaved fragment containing the neo-binding-site is labeled. After a sufficient amount of time to allow for binding, the unbound components can optionally be removed or washed away and any remaining labeled binding molecule is detected. A higher amount of signal from the label correlates with a higher amount of protease activity.

Figure 1G:
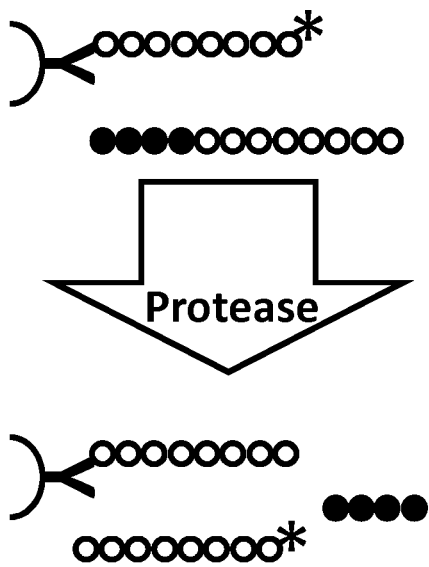

The format depicted in FIG. 1G differs from FIG. 1E in that it is a competitive format which includes an uncleaved substrate and a labeled first molecule comprising an exposed neo-binding-site. A binding molecule that preferentially binds a neo-binding-site is bound or attached to a surface. If the sample contains protease activity, the unbound substrate is cleaved which exposes the substrate's neo-binding-site. This allows the cleaved substrate to compete with the exposed neo-binding-site of the first molecule for binding of the anti-neo-binding-site binding molecule. After a sufficient amount of time to allow for binding, the unbound components can optionally be removed or washed away and any remaining labeled binding molecule is detected. In this case, a lower amount of signal from the label correlates with a higher amount of protease activity.

Figure 1H:
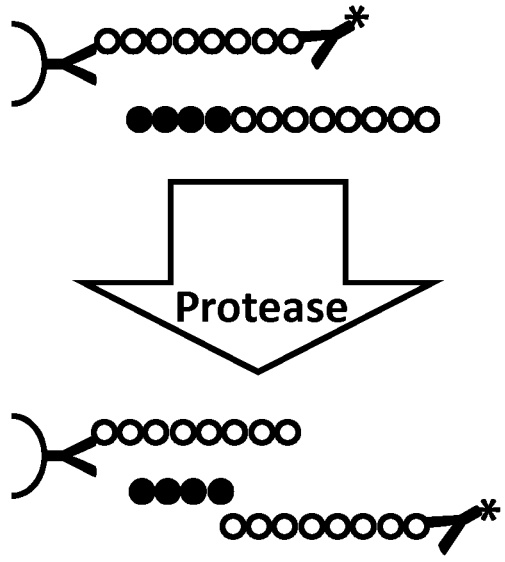

The format depicted in FIG. 1H includes an uncleaved substrate, a first molecule (competitor molecule) comprising an already exposed neo-binding-site, an anti-neo-binding-site binding molecule attached or bound to a surface and a labeled binding molecule wherein the binding molecule binds the first molecule. In some embodiments, the labeled binding molecule preferentially binds the first molecule as compared to the cleaved and/or uncleaved substrate. In some embodiments, the labeled binding molecule does not bind the cleaved and/or uncleaved substrate. In some embodiments, the labeled binding molecule binds a site present in the competitor molecule, but not present in the cleaved and/or uncleaved substrate.

Figure 1I:
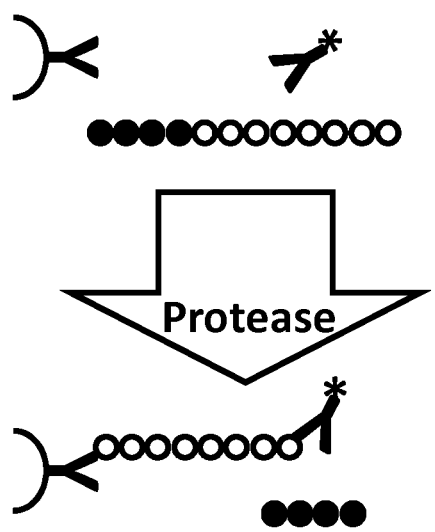
FIG. 1I depicts a format that uses an anti-metatype binding molecule. The anti-metatype binding molecule can be either the capture binding molecule (depicted as attached or bound to a surface) or the labeled binding molecule.
Figure 2A:
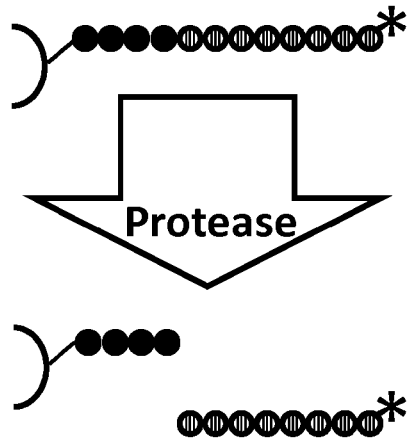
FIG. 2A utilizes a labeled substrate that is bound to a surface at a point(s) in the substrate that is N-terminal to the cleavage site and a label(s) is bound at a point(s) C-terminal to the cleavage site.
Figure 2B:
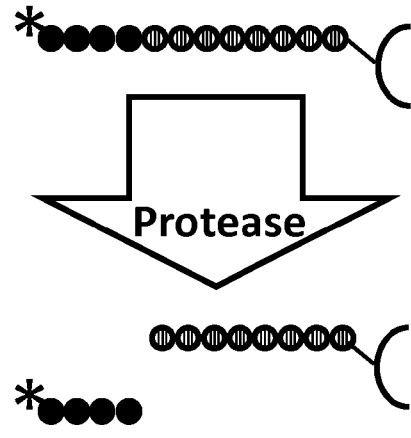
FIG. 2B utilizes a labeled substrate that is bound to a surface at a point(s) in the substrate that is C-terminal to the cleavage site and a label(s) is bound at a point(s) N-terminal to the cleavage site.
Figure 2C:
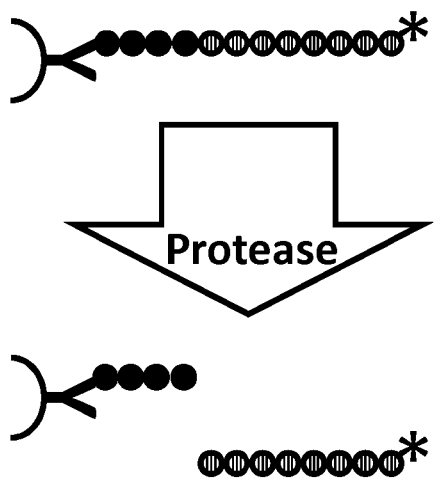
FIG. 2 depicts various assay formats for detecting protease activity.
Figure 2D:
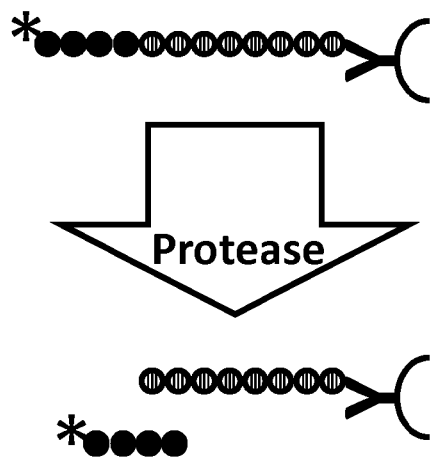

The format depicted in FIG. 1I includes an uncleaved substrate, a first binding molecule and a second binding molecule. In this format, the first binding molecule can bind the cleaved substrate and the second binding molecule is an anti-metatype binding molecule. The anti-metatype binding molecule preferentially binds the complex comprised of the cleaved substrate bound to the first binding molecule as compared to binding to either the cleaved substrate or first binding molecule alone. Either the first binding molecule or the second binding molecule can be the detector (e.g., labeled) binding molecule, with the other binding molecule being the capture binding molecule that is attached or bound or capable of being attached or bound to a surface.

The formats listed in FIG. 1 are presented only to illustrate various non-limiting examples of formats that can be used in accordance with the invention and the various assay formats in FIG. 1 can be modified in accordance with the invention. For example, where a molecule is bound or attached to surface, the binding or attachment can be direct attachment, such as a covalent bond or through a binding interaction of binding partners such as an antibody to an epitope or streptavidin to biotin. For example, an antibody (or other binding molecule) may be attached to a surface by attaching one member of a binding pair (e.g., biotin) to the antibody and the other member of the binding pair (e.g., streptavidin) being attached to the surface Additionally, where the binding is depicted as direct it could also be indirect such as through a third binding molecule. For example, instead of using a labeled binding molecule (e.g., a labeled antibody) that binds a particular binding site (e.g., an epitope) an unlabeled binding molecule (e.g., primary antibody) can bind the particular binding site and a labeled binding molecule (e.g., secondary antibody) that binds the unlabeled binding molecule can be utilized, typically with similar results. A similar approach can be used for attaching or binding a first binding molecule to a surface, such as a bead or a plate. For example, a first binding molecule, substrate or molecule with an exposed neo-binding-site can be directly or indirectly attached to a surface. Direct attachment could be covalent attachment. Indirect attachment can be accomplished, for example, by utilizing a "secondary" binding molecule. For instance, a secondary binding molecule is bound or attached to a surface and this secondary binding molecule binds the first binding molecule, the substrate or the molecule with an exposed neo-binding site. In some embodiments, a surface may comprise one partner of a binding pair (such as avidin or biotin) and the molecule to be bound contains the other binding partner. For example, in some embodiments, a surface comprises streptavidin (e.g., streptavidin coated microparticles or beads) and a binding molecule or substrate comprises biotin for attachment to the surface.

A capture binding molecule, e.g., as depicted in FIGS. 1C-1I may be present during the reaction to detect an enzymatic activity (e.g., protease activity) or may be contacted with any reaction products after or during the reaction. Additionally, a capture binding molecule may be bound or attached to a surface at the time it is contacted with any reaction products or may be bound or attached to a surface after being contacted with any reaction products.

In some embodiments, a substrate may be reacted with a sample in the presence of some, all or none of the binding molecules required or utilized for a particular format.

Different formats of the assay, e.g., those depicted in FIG. 1, can be performed by combining components in any way that still results in detection of the activity of the sample. For example, for many embodiments of the invention a substrate could be reacted with a sample and any necessary components for the activity (e.g., protease activity) and then the reaction could be combined with a binding molecule(s) required for a particular format. In the alternative, a sample could be initially reacted with all of the required assay components being present including one or more binding molecules. Additionally, some assay formats of the invention utilize a binding molecule attached or bound to a surface. In some embodiments, this binding molecule is present in the reaction with a sample and then this binding molecule is attached or bound to a surface. In some embodiments, this binding molecule is bound to a surface prior to, during or after the reaction with a sample.

Additionally, the formats shown in any of FIG. 1 could be modified so that an anti-neo-binding-site binding molecule is not labeled with a detectable label and wherein the assay contains an additional labeled binding molecule that binds the anti-neo-binding-site binding molecule. For example, wherein the anti-neo-binding-site binding molecule is an antibody of a first species and the additional labeled binding molecule is an antibody that binds the antibody or antibodies of the first species.

Additionally, it is understood that a labeled molecule, such as a binding molecule or substrate, can have one or more labels attached and/or associated with it. In some embodiments, more than one label per molecule may increase the sensitivity of an assay.

It is also understood that substrates could contain more than one cleavage site per molecule. These molecules may contain more than one neo-binding-site resulting from cleavage of more than one cleavage site. Also, a substrate or the invention may have a cleavage site that when cleaves can result in more than one neo-binding-site. These substrates could be utilized in assays that use one type of binding molecule that binds to one of the neo-binding-sites or in assays that use more than one type of binding molecule, where each type binds more than one neo-binding-site.

Assays of the invention can be, but are not limited to, immunoassays.

Various embodiments of the invention utilize molecules or binding molecules bound or attached to a surface. Surfaces that can be used with these embodiments include, but are not limited to, a glass surface (e.g., a glass slide or bead), a plastic surface, a bead, a metal surface, a polystyrene surface (e.g., a bead or a plate), a nitrocellulose surface, or a nano-particle surface. A bead can be essentially any shape that is compatible with the particular assay format. In some embodiments, a bead is round or oval. In some embodiments, a bead can be a paramagnetic bead, a magnetic bead, a latex bead, a glass bead, a plastic bead and/or a superparamagnetic bead. In some embodiments, a bead is coated with streptavidin or biotin.

Some substrates of the invention comprise a general formula selected from the group consisting of:

$X_1$-CS-NBS-$X_2$; $X_1$-NBS-CS-$X_2$; $X_1$-CS-$X_3$-NBS-$X_2$; and $X_1$-NBS-$X_3$-CS-$X_2$; where $X_1$=an amino acid sequence comprising from 0 to 500; 0 to 100; 0 to 50; 0 to 15; 0 to 10; or 0 to 5 amino acids;

CS=a cleavage site;

NBS=a neo-binding-site;

$X_2$=an amino acid sequence comprising from 0 to 500; 0 to 100; 0 to 50; 0 to 15; 0 to 10; or 0 to 5 amino acids; and $X_3$=an amino acid sequence comprising from 0 to 100; 0 to 50; 0 to 15; 0 to 10; or 0 to 5 amino acids.

In some embodiments of the invention, FXa activity is detected using a substrate that comprises a FXa recognition site, wherein cleavage at the cleavage site generates/exposes a neo-binding-site. A FXa recognition site, also referred to herein as a FXa cleavage site, can be the amino acid sequence IEGR (SEQ ID NO:1). The IEGR (SEQ ID NO:1) amino acid sequence is used herein as an exemplary FXa cleavage site, but other FXa cleavage sites, such as IDGR (SEQ ID NO:39) and AEGR (SEQ ID NO:40), can be used in the same manner. Therefore, any time IEGR (SEQ ID NO:1) is utilized, the invention also contemplates that another FXa cleavage site, such as IDGR (SEQ ID NO:39) and AEGR (SEQ ID NO:40), could be utilized.

In some embodiments of the invention, FXa activity is detected using a peptide (e.g., sequence V (below)) which comprises a FXa recognition site (-IEGR-) (SEQ ID NO:1) at the N-terminal of the peptide sequence -DYKDDDDKGS- (SEQ ID NO:4; contains a FLAG® epitope), a linker/spacer sequence -GSHHHHHH(mPeg2)- (SEQ ID NO:7) and a lysine conjugated with a biotin on the side chain at its C-terminus. FXa cleavage of the peptide bond after the arginine residue of the -IEGR- sequence (SEQ ID NO:1) leaves an N-terminal neo-binding-site (sequence IV). The peptide sequence V can be captured by streptavidin coated beads (e.g., M280-SA beads (Invitrogen, Cat: 112-06D)) through the high affinity interaction of biotin and avidin. A neo-binding-site produced as a result of FXa activity can quantitatively be detected by an anti-neo-binding-site binding molecule, such as a TAG Plus anti-FLAG® M1 antibody (e.g., see Example 2).

Peptide sequence IV.
(SEQ ID NO: 4)
NH₂-DYKDDDDKGS-

Peptide sequence V.
(SEQ ID NO: 8)
Bz-IEGRDYKDDDDKGSHHHHHH(mPeg2)(KLCBiot)-amide.

The Bz (Benzyol) is a protective group commonly employed in chemical synthesis and does not interfere with the cleavage of the peptide at IEGR (SEQ ID NO: 1).

In some embodiments, mPeg2, a mini-polyethylene molecule which provides a hydrophilic 9-atom spacer, is inserted, e.g., as a spacer, between the peptide cleavage sequence and a biotin molecule, which can become "trapped" deep in the binding pockets of a streptavidin molecule and may cause steric hindrance for the cleavage of IEGR sequence (SEQ ID NO: 1). For example, see Examples 1 and 4 below.

KLCBiot is an abbreviation for Lysine-Long-Chain-Biotin. A biotin molecule is put on the side chain primary amine of lysine (at the end of the sequence) with a biotin modification reagent (Biotin-Long-Chain NHS ester).

In some embodiments of the invention, FXa activity can be detected with a competitive immunoassay for detecting FXa activity using a peptide (e.g., peptide sequence VI) comprising a FXa recognition site (-IEGR-) (SEQ ID NO:1) N-terminal to the peptide sequence IV-amide (DYKDDDDKGS-amide) (SEQ ID NO:4). The FXa cleavage of the peptide bond after the arginine residue of the -IEGR- sequence (SEQ ID NO:1) in peptide sequence VI leaves an N-terminal neo-binding-site (sequence IV), which can be measured, for example, with a TAG conjugated peptide sequence VII and a capture anti-FLAG® M1 antibody in a competitive immunoassay format. A decrease in signal correlates with an increase in FXa activity.

Peptide sequence VI.
(SEQ ID NO: 5)
NH₂-IEGRDYKDDDDKGS-amide

Peptide sequence VII.
(SEQ ID NO: 4)
NH₂-DYKDDDDKGS-TAG Plus

In some embodiments of the invention, FXa activity can be detected with an assay to detect a labeled molecule with a neo-binding-site. For example, an assay for detecting FXa activity can utilize a peptide (e.g., peptide sequence VIII) which comprises a FXa recognition site (-IEGR-) (SEQ ID NO:1) N-terminal to the peptide sequence DYKDDDDKGS-TAG (SEQ ID NO:4). FXa cleavage of the peptide bond after the arginine residue of the -IEGR-sequence (SEQ ID NO:1) produces a peptide with the neo-binding-site (sequence IV) at its N-terminus and with TAG at its C-terminus. The cleaved TAG labeled substrate can be captured by a capture antibody that binds the neo-binding-site of the cleaved labeled substrate.

Peptide sequence VIII.
(SEQ ID NO: 5)
NH₂-IEGRDYKDDDDKGS-TAG

Some embodiments of the invention provide a method of detecting FXa activity by detecting a neo-binding-site using a sandwich assay format. For example, the peptide sequence IX (below) can be used. FXa cleavage of the peptide bond after the arginine residue of -IEGR- sequence (SEQ ID NO:1) of peptide sequence IX produces the neo-binding-site (sequence IV). This neo-binding-site can be captured by a specific antibody such as anti-FLAG® M1 antibody to form a peptide antibody complex, which can be detected by a labeled detector antibody which specifically or preferentially binds to the peptide antibody complex.

Peptide sequence IX.
(SEQ ID NO: 5)
Bz-IEGRDYKDDDDKGS-amide

For the some of the aforementioned formats "TAG" or "TAG Plus" is used as an exemplary type of label. However, any compatible label type could be utilized in these assays. Examples of various label types are discussed herein.

The chemical structure of TAG NHS ester (Ruthenium (II) tris-bipyridine NHS ester) is:

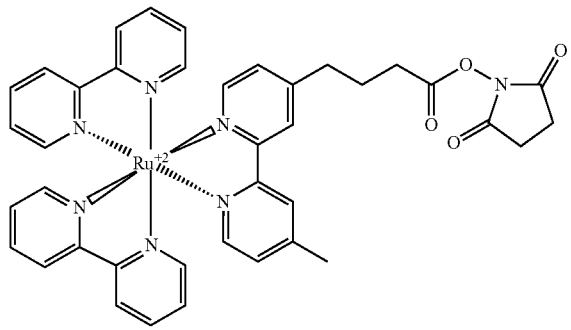

The chemical structure of TAG Plus NHS ester is:

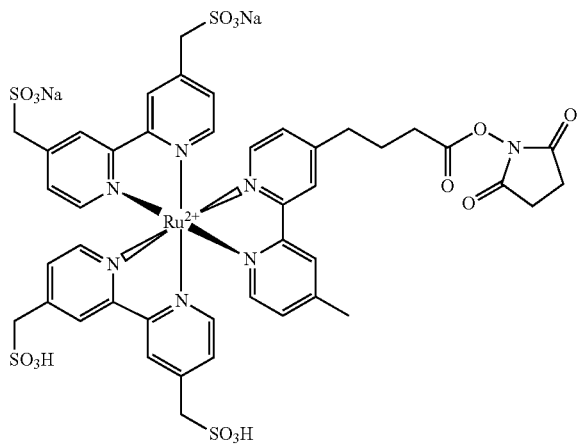

It is understood that substrates for FXa, disclosed herein, could have additional amino acids present on the N-terminus, C-terminus or both the N-terminus and C-terminus of the amino acid sequence.

The invention also provides methods for detecting caspase activity. The present invention can be, inter alia, utilized to detect and/or measure caspase protease activity in a sample.

Variations in levels of caspases or caspase activity have been shown in patients with various diseases, including, but not limited to, (i) cancer, e.g., melanoma (Mouawad et al. Melanoma Res. (2002) 12(4):343-8), cervical (Babas et al. International Journal of Gynecological Cancer (2010) 20(8): 1381-1385), hepatocellular carcinoma; renal (Messai et al. Int J. Oncol. 2010 36(5):1145-54); (ii) heart disease, e.g., myocardial infarction (Agosto et al. J Am Coll Cardiol (2011) 57:220-221); (iii) Chronic obstructive pulmonary disease (COPD) (Hacker et al. Journal of Clinical Laboratory Analysis (2009) 23(6):372-379); and (iv) liver disease, such as hepatitis C infection (Bantel et al. Hepatology, (2004) 40(5): 1078-1087), hepatitis B infection (Papatheodoridis et al. Gut (2008) 57:500-506), chronic liver disease, hepatitis, viral hepatitis, alcoholic hepatitis, nonalcoholic fatty liver disease and cholestatic liver disease.

Caspases cleave at various sites or amino acid sequences, e.g., see the review articles Fischer et al. (Cell Death and Differentiation 2003 10:76-100) and Caulin et al. (Journal of Cell Biology (1997) 138:1379-1394). In epithelial cells, the intermediate filament cytokeratin 18 (CK-18) represents one of the major caspase substrates and is typically present in abundant quantities. Initial cleavage by caspase-6 cleaves the full-length CK-18 to an N-terminal fragment and C-terminal fragment. The amino acid sequence DALD (SEQ ID NO:18) at original position Asp396 provides the substrate for caspases-3, -7, and -9, but is not recognized by caspase-6.

Caspases are also known to modulate cytokines. For example, caspase-3 converts pro-IL-16 to bioactive IL-16 by cleaving at the SSTD (SEQ ID NO:21) amino acid sequence in IL-16.

A caspase substrate of the invention can have a wild-type caspase cleavage site or a non-native or engineered caspase cleavage site. For example, Ku et al. (J. Biol. Chem. (2001) 279:26792-26798) shows that wild-type cleavage sites can be modified or changed but maintain an ability to be cleaved by a caspase. Caspases cleave their substrates after aspartate residues Amino acid sequences of caspase cleavage sites which can be utilized in the invention include, but are not limited to, DEVD (SEQ ID NO:13), IETD (SEQ ID NO:14), VDVAD (SEQ ID NO:15), VEID (SEQ ID NO:16), YVAD (SEQ ID NO:17), DALD (SEQ ID NO:18), VEVD (SEQ ID NO:19), VEMD (SEQ ID NO:20), SSTD (SEQ ID NO:21) and WEHD (SEQ ID NO:22, for caspase 1, 4 and/or 5). Therefore, some substrates of the invention may comprise a caspase cleavage site selected from the group consisting of SEQ ID NOs:13-22

The following are examples of amino acid sequences that can comprise substrates that use a FLAG® epitope and a caspase cleavage site for detecting caspase activity/cleavage. (The FLAG® epitope is used here only as an exemplary binding site that could be used.)

```
                                          (SEQ ID NO: 10)
DALDDYKDDDDK,
e.g., for caspase 3, 7 and/or 9

(SEQ ID NO: 11)
VEVDDYKDDDDK,
e.g., for caspase 3, 6 and/or 7

(SEQ ID NO: 12)
VEMDDYKDDDDK,
e.g., for caspase 6

(SEQ ID NO: 25)
SSTDDYKDDDDK,
e.g., for caspase 3

(SEQ ID NO: 26)
DEVDDYKDDDDK (SEQ ID NO: 27)
IETDDYKDDDDK (SEQ ID NO: 28)
VDVADDYKDDDDK (SEQ ID NO: 29)
VEIDDYKDDDDK (SEQ ID NO: 30)
YVADDYKDDDDK (SEQ ID NO: 31)
WEHDDYKDDDDK
```

It is understood that substrates for caspase(s), disclosed herein, could have additional amino acids present on the N-terminus, C-terminus or both the N-terminus and C-terminus of the amino acid sequence.

Ku et al. (J. Biol. Chem. (2001) 279:26792-26798) shows that the sequences VEVDD (SEQ ID NO:23) and VEMDD (SEQ ID NO:24) can both be cleaved by a caspase(s), e.g., see Table 1 of Ku et al.

Some embodiments of the invention utilize an anti-metatype binding molecule (e.g., an antibody). Assays involving an anti-metatype binding molecule are sometimes referred to as single epitope sandwich assays. Anti-metatype binding molecules are molecules that preferentially bind a complex comprising a binding molecule bound to another molecule. For example, a first binding molecule binds an antigen and the anti-metatype binding molecule preferentially binds the complex comprised of the first binding molecule and the antigen as compared to binding of the anti-metatype binding molecule to either of the first binding molecule alone or the antigen alone. Anti-metatype binding molecules, methods for making them and/or assays utilizing them are described in Tamm et al. (Clinical Chemistry (2008) 54:1511-1518); Voss et al. (Mikrochim Acta (1997) 126:193-202); Kim et al. (Anal. Biochem. (2009) 386:45-52); and U.S. Patent Publication No. 20100203560.

In some embodiments of the invention, an anti-metatype binding molecule can be utilized for capture or detection. For example, the invention includes an assay format utilizing a substrate comprised of a cleavage site, wherein cleavage of the substrate allows a first binding molecule to bind a neo-binding-site (e.g., a neoepitope). In some embodiments, the neo-binding-site is heterologous to the cleavage site. After the complex comprised of the first binding molecule bound to the neo-binding-site is formed, the complex is bound by an anti-metatype binding molecule. In some embodiments, an anti-metatype binding molecule can be used as either a detector or capture molecule in a sandwich type assay. In some embodiments, an anti-metatype binding molecule can be labeled. In some embodiments, an unlabeled anti-metatype binding molecule can also be used as a detector binding molecule and a labeled secondary binding molecule that binds the anti-metatype binding molecule can be used for detection of the binding of the anti-metatype binding molecule to the complex. In some embodiments, an anti-metatype binding molecule is used as a capture binding molecule.

Assay formats using an anti-metatype binding molecule can be set-up the same or similar to the format depicted in FIG. 1I with either the capture binding molecule or the labeled binding molecule being an anti-metatype binding molecule, where the anti-metatype binding molecule preferentially binds the complex of the other binding molecule bound to the cleaved substrate as compared to binding to either of the other binding molecule or cleaved substrate alone. Assays formats utilizing an anti-metatype, in some embodiments, will be able to effectively use shorter incubation times because the anti-metatype binding molecule is specific for the binding complex, allowing high concentrations of substrate to be used in the assay which shorten the required incubation time, thereby shortening the total length of time for the assay to be performed.

Anti-metatype binding molecules include, but are not limited to, antibodies, peptides, aptamer, cyclic peptides and phage peptides, e.g., see Kim et al. (Anal. Biochem. (2009) 386:45-52). In some embodiments, an anti-metatype binding molecule is an antibody (e.g., a monoclonal antibody) that preferentially binds the complex of a second antibody bound to a cleaved substrate as compared to binding to either of the unbound second antibody or the cleaved substrate not bound to the second antibody.

Some embodiments of the invention do not utilize an anti-metatype binding molecule.

In some embodiments of the invention, e.g., where FXa activity is detected, the assay can also include the use of a thrombin inhibitor. Thrombin is produced by the enzymatic cleavage of two sites on prothrombin by activated FXa. Thrombin activates factor XI. Activities of some anti-coagulation factors can be measured by including a thrombin inhibitor, such as the antithrombin III, in the assay. To stop FXa generation and inhibit thrombin a thrombin inhibitor may be used with some embodiments of the invention. For example, some embodiments of the invention comprise a first reaction with a sample that will produce FXa if the sample comprises a certain protein, enzyme or activity such as FVIII, e.g., see Example 8. After incubation of the first reaction under proper conditions, a thrombin inhibitor can be added, for example at the same time a substrate is added. Thrombin inhibitors that might be used in the invention include, but are not limited to, hirudin, bivalirudin, lepirudin, desirudin, argatroban, melagatran, ximelagatran, dabigatran, I-2581 (e.g., DiaPharma Group Inc. West Chester, Ohio 45069), anti-thrombin (e.g., human antithrombin) and heparin.

In some embodiments of the invention, e.g., where FXa activity is detected, the assay may also include the use of a thrombin. This includes assays for coagulation factors that can be detected or measured through detection of FXa activity such as FVIII, FIX, factor VII (FVII) or FXI.

In some embodiments, the assay includes the use of a Gly-Pro-Arg-Pro amide (GPRP-NH$_2$; SEQ ID NO:32). In some embodiments, GPRP-NH$_2$ (SEQ ID NO:32) is utilized to block the formation of fibrin network which can interfere with particular assay types or formats, such as those using beads (e.g., immunoassay formats).

In some embodiments, the assay includes the use of a calcium source such as CaCl$_2$. The calcium source may be added to the assay at various steps. The particular step can be determined by those skilled in the art based on the assay and/or the assay format. For example, some antibodies, such as the ANTI-FLAG® M1 antibody bind better in the presence of calcium. Some reactions may be inhibited or increased by the presence of calcium. In some assays this may not be an issue, whereas for others it may influence the results. For example, for assays measuring a reaction that may be influenced by the presence of calcium, calcium can be added at a time point after the reaction has had a chance to occur if calcium is necessary or desired for a particular step such as antibody binding.

Depending on the particular assay and activity to be detected, the following are examples of concentrations that may be used: factor IXa at a concentration from 0.001 µM to 10 µM or from 0.01 to 0.2 µM; factor VIII or factor VIIIa at a concentration from 0.01 to 10 U/mL or from 0.2 to 1.0 U/mL; thrombin at a concentration from 0.1 nM to 100 nM; FX or factor Xa at a concentration from about 0.01 µM to about 5.0 µM, from about 0.05 µM to about 1.0 µM, or at about 0.2 µM; phospholipids at from about 100 µM to about 400 µM or from about 100 µM to about 1.0 mM; calcium at a concentration from about 0.01 mM to about 100 mM or from about 1 mM to about 20 mM.

In some embodiments, an assay to detect a particular enzymatic activity, such as protease activity, of a sample can also be performed with control samples. Control samples can contain known amounts of a particular enzyme or activity including samples with no enzyme or activity. In some embodiments, an assay to detect an enzymatic activity involves performing the assay on a sample with an unknown amount of enzymatic activity and on samples with known amounts of enzymatic activity. In some embodiments, the control samples are used to create a standard curve which can be used to quantitate the amount of activity or enzyme in a sample with an unknown amount.

Binding Molecules

Binding molecules of the invention are molecules that can bind to a desired site and include, but are not limited to, antibodies, peptides, lectins, aptamers and monobodies (also known as ADNECTINS™).

Essentially any type of antibody may be utilized as a binding molecule in accordance with the present invention. These include, but are not limited to, synthetic antibodies, monoclonal antibodies, recombinantly produced antibodies, intrabodies, multispecific antibodies, bispecific antibodies, human antibodies, humanized antibodies, chimeric antibodies, synthetic antibodies, single-chain Fvs (scFv), Fab fragments, F(ab') fragments, disulfide-linked Fvs (sdFv), anti-metatype antibodies and epitope-binding fragments of any of the above. Antibodies used in the present invention include immunoglobulin molecules and portions of immunoglobulin molecules capable of binding the desired binding site. The immunoglobulin molecules of the invention can be essentially of any class, isotype (e.g., IgG, IgE, IgM, IgD, IgA and IgY) or subclass (e.g., IgG1, IgG2, IgG3, IgG4, IgA1 and IgA2) of immunoglobulin molecule.

Antibodies or antibody fragments may be from any species, may be chimeric antibodies or humanized antibodies. In some embodiments, an antibody is a human antibody. Also, camelid antibodies that naturally lack a light chain can be used. Structures known as nanobodies and domain antibodies can be used, including polypeptides comprising a single CDR of an antibody known to bind the cognate binding site, so long as an effective amount of the binding ability is retained.

An antibody(s) utilized in the present invention can be prepared essentially using any technique known in the art. For example, an animal can be immunized or challenged, according to an appropriate immunization schedule, with a protein or peptide, e.g., comprising an exposed neoepitope. In some cases, a neoepitope is coupled to a carrier molecule such as bovine serum albumin (BSA), keyhole limpet hemocyanin (KLH), ovalbumin (OVA), thyroglobulin (TG) or synthetic carriers such as multiple antigenic peptides (MAPS) to enhance antibody responses and/or to improve recognition. After a suitable time period, antibodies are extracted and/or isolated from the animal. Antibodies can be obtained from, for example, ascites fluid, blood, serum, or monoclonal antibodies can be obtained from the fusion of spleen cells with a partner cell line. Other methods for generating desired antibodies are known in the art, e.g., utilizing display techniques such as phage display (e.g., see U.S. Pat. No. 7,118,879). Antibodies have numerous amino, carboxyl and sulfhydryl groups that might be utilized for coupling reactions. Monoclonal or polyclonal antibodies can be screened, e.g., for those that specifically bind a molecule with an exposed neoepitope as compared to binding to a molecule where the neoepitope has not been exposed or created, e.g., by cleavage of the molecule.

Some embodiments of the invention utilize a binding molecule (e.g., an antibody) that specifically or preferentially binds a N-terminal or C-terminal epitope as compared to binding to the same "epitope" that is not N-terminal or C-terminal, respectively. Epitopes that antibodies can preferentially bind at the N-terminus include, but are not limited to, the amino acid sequence DYKDDDDK (SEQ ID NO:2); DIPEN (SEQ ID NO:33); ARG (SEQ ID NO:34); ARGSV (SEQ ID NO:35); ARGSVIL (SEQ ID NO:36); and FFGV (SEQ ID NO:37). An example of an epitope that an antibody can preferentially bind at the C-terminus is amino acid sequence TEGE (SEQ ID NO:38). Examples of antibodies that preferentially bind N-terminal or C-terminal amino acid sequences can be obtained from, e.g., MD Bioproducts (St Paul, Minn.) and include catalog nos. 1042002, 1042001, 1028023, 1042004 and 1042003. These N-terminal or C-terminal epitopes can be used in conjunction with protease cleavage sites to detect activity of a particular protease. For example, the invention includes a substrate containing a cleavage site selected from IEGR (SEQ ID NO:1), DEVD (SEQ ID NO:13); IETD (SEQ ID NO:14); VDVAD (SEQ ID NO:15); VEID (SEQ ID NO:16); YVAD (SEQ ID NO:17); DALD (SEQ ID NO:18); VEVD (SEQ ID NO:19); VEMD (SEQ ID NO:20); SSTD (SEQ ID NO:21); WEHD (SEQ ID NO:22); VEVDD (SEQ ID NO:23); and VEMDD (SEQ ID NO:24), immediately N-terminal to an amino acid sequence selected from DYKDDDDK (SEQ ID NO:2), DIPEN (SEQ ID NO:33); ARG (SEQ ID NO:34); ARGSV (SEQ ID NO:35); ARGSVIL (SEQ ID NO:36); and FFGV (SEQ ID NO:37).

In some embodiments, the antibody is a monoclonal antibody secreted by the murine hybridoma 4E11 (ATCC HB 9259) and that binds the site DYKDDDDK (SEQ ID NO:2). Murine hybridoma 4E11 (ATCC HB 9259) is described in U.S. Pat. Nos. 4,851,341 and 5,011,912. The epitope DYKDDDDK (SEQ ID NO:2) is described in U.S. Pat. Nos. 4,703,004; 4,782,137; 4,851,341; and 5,011,912.

Aptamers can be made using methods known in the art, e.g., as described in U.S. Pat. No. 5,789,157. Lectins, and fragments thereof, can be made using methods known in the art or those commercially available.

In some embodiments, a binding molecule of the present invention is an aptamer. Aptamers are nucleic acid sequences that, similar to antibodies, bind to a target molecule. Aptamers can be used in similar ways as described herein for antibodies or binding molecules.

In some embodiments, a binding molecule of the invention is a monobody (also known as an ADNECTIN™), e.g., see U.S. Pat. No. 7,115,396. Monobodies are a class of targeted biologics that are derived from fibronectin.

Detection or Measurement of a Molecule's Activity

Assays of the invention can detect a molecule's activity, such as protease activity, either directly or indirectly. For example, direct detection of a protease could be performed by detecting a neo-binding-site that is exposed or created by the protease activity of interest. For instance, if FXa activity is to be measured, FXa itself can cleave a substrate and exposes a neo-binding-site, which can be detected. Indirect detection of a first molecule can involve detecting the activity of a second molecule where the second molecule's activity is influenced or correlates with the activity of the first molecule. This includes using the detection of down-stream protease activity to correlate to the activity of an upstream activity, such as a second protease that acts upstream of the down-stream protease in a particular cascade/pathway. For example, FVIII activity can be detected indirectly by measuring FXa activity, e.g., as described herein.

Some assays of the invention detect or measure FXa activity. FXa based assays, e.g., as described herein, can be integrated into assays for measuring several coagulating factors which can be detected through the production of FXa from mixtures of factor cocktails. Coagulating factors that can be detected or measured through detection of FXa activity include, but are not limited to, FVIII, FIX, FVII, FXI and heparin.

Some assays of the invention detect or measure activity of a caspase(s). Caspases recognize and cleave distinct sites and result in the generation of neo-binding-sites, which can be qualitatively or quantitatively measured, e.g., by immunoassays.

As discussed above various assay formats are encompassed by the invention. These formats can be combined with various detection labels and related detection methods. For example, detection labels that can be utilized in the invention are those that are compatible with an assay format of the invention and include, but are not limited to, a ruthenium metal chelate, an osmium metal chelate, an electrochemiluminescent label, a fluorophore, an enzymatic label, a latex particle, a magnetic particle, a radioactive element, a phosphorescent dye, a dye crystalite, a gold particle, a silver particle, a selenium colloidal particle, a metal chelate, a coenzyme, an electro active group, an oligonucleotide, a stable radical and an enzyme label such as horseradish peroxidase and alkaline phosphatase. In some embodiments, a detection label can be a ruthenium-containing or osmium-containing luminescent organometallic compound (e.g., see U.S. Pat. No. 5,310,687).

The assays of the invention can be performed utilizing any assay type that is compatible with an assay format of the invention, e.g., electrochemiluminescence (ECL) assays and ELISA assays.

An overview of ECL assays is provided in Mathew et al. (Kathmandu University Medical Journal, 2005, 3:91-93) and Forster et al. (Annu Rev Anal Chem. 2009, 2:359-85). ECL can be utilized for detection. ECL or electro generated chemiluminescence is a form of chemiluminescence in which the light emitting chemiluminescent reaction is preceded by an electrochemical reaction. The electrochemical reaction can allow the time and/or position of the light emitting reaction to be controlled. By controlling the time, light emission can be delayed until a certain desired event(s) has occurred, such as an enzymatic reaction, protease cleavage and/or binding of one molecule to another. Control over position can be used to confine light emission to a region which is precisely located with respect to the detector, improving sensitivity by increasing the ratio of signal to noise.

Some ECL based assays of the invention can involve (i) a capture step, which includes the use of a binding molecule (capture agent) bound or attached to a surface having an incorporated electrode, and (iii) a detection step, which uses a detection agent coupled to an ECL label. An ECL label provides light emission generated from a chemiluminescent reaction stimulated by an electrochemical reaction. ECL labels are also commonly referred to as TAGs. Commonly used ECL labels include, but are not limited to, organometallic compounds where the metal is from, for example, the noble metals of group VIII, including Ru-containing and Os-containing organometallic compounds such as the Ru(2, 2'-bipyridine)32+ moiety (also referred to as "Rubpy" or "TAG1", see, e.g., U.S. Pat. No. 5,238,808). Also, derivatives of TAG1 and Rubpy can be used as ECL labels. ECL-based detection systems utilize an electrical potential to excite an ECL label to emit light. An electrical wavelength is applied across an electrode surface, e.g., a metal surface, and a counterelectrode (see e.g., U.S. Pat. Nos. 5,068,088, 5,093,268, 5,061,445, 5,238,808, 5,147,806, 5,247,243, 5,296,191, 5,310,687, 5,221,605 and 6,673,533). An ECL label is promoted to an excited state as a result of a series of chemical reactions triggered by the electrical energy received from the working electrode. In some embodiments, a molecule, such as, oxalate or tripropylamine, is added during a detection method which promotes the chemical reaction and consequently results in the emission of measurable light from the ECL label. Various ECL labels are known in the art such as those available from Meso Scale Discovery (Gaithersburg, Md.).

In some embodiments utilizing ECL, a preparation of biotin and/or ruthenium (e.g., BV-TAG Plus or BV-TAG) modified protein (e.g., an antibody) conjugates are used and, for example, can be obtained through the modification of primary amine groups (—$NH_2$) using NHS-ester biotin and BV-TAG Plus NHS Ester or BV-TAG NHS Ester. Some ECL analyzers detect light emitted from paramagnetic beads-coupled to ruthenium on its platinum electrode (e.g., inside the flow cell) when a voltage is applied. The light is detected using a photodiode detector and its intensity is proportional to the amount of ruthenium label on the bead surface. Depending on the particular format, the amount of light detected may be directly or inversely proportional to a particular activity, such as FXa activity.

In some embodiments of the invention, a detection method (e.g., an ECL based method) may include a wash step, e.g., after the addition of a capture binding molecule, after the addition of a sample, or after addition of a labeled molecule. In some embodiments, a wash step is performed after each step of the detection method. In some embodiments, a wash step is performed as the last step prior to detection. A wash step can be used to remove, or wash away, any unbound molecules/components such as capture binding molecules, components/molecules of a sample, substrate or labeled detection molecules. A wash step is typically performed using a wash buffer. In some embodiments, a wash buffer includes a surfactant, an acid, a base salt solution or any combination thereof.

In one embodiment, the present invention is an ECL detection kit for detecting activity of a sample including, but not limited to, caspase, FVII, FVIII, FIX, FXa or heparin activity. In some embodiments, a kit includes (i) a binding molecule (e.g., an antibody) optionally immobilized or bound to a surface (e.g., containing an electrode) and (ii) a labeled binding molecule or a labeled substrate. In some embodiments, a kit includes an unlabeled binding molecule, a substrate of the invention and a labeled binding molecule. In some embodiments, the labeled binding molecule binds a neo-binding-site. In some embodiments, the kits comprise an ECL labeled substrate or an ECL labeled binding molecule. In some embodiments, a kit can be used in combination with a portable ECL analyzer. Examples of ECL analyzers which can be used include, but are not limited to, BioVeris' M-SERIES® MIM analyzer (BioVeris, Gaithersburg, Md.) and Meso Scale Discovery's Sector Imager 6000, Sector Imager 2400, Sector PR 400 and Sector PR 100.

EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

Whereas, particular embodiments of the invention have been described herein for purposes of description, it will be appreciated by those skilled in the art that numerous variations of the details may be made without departing from the invention as described in the appended claims.

Example 1

Detecting FXa Activity with Biotin- and TAG Plus-Conjugated Substrate

FXa activity can be measured through the use of peptides that include a FXa recognition sequence, a biotin at one terminus of the peptide and a BV-TAG Plus at the other terminus. In this embodiment, FXa recognizes and specifically cleaves the peptide between the arginine amino acid and the next amino acid toward the carboxy terminus, e.g., between arginine and glycine in peptide probe sequences I and II below. The cleavage by FXa results in the separation of biotin from the BV-TAG Plus. When the biotin is captured with streptavidin coated microparticles (Dynabeads M280-SA, Invitrogen, Cat: 112-06D), this loss of BV-TAG Plus can be measured quantitatively by an ECL instrument such as the M-SERIES® M1MR Analyzer (BioVeris Corporation, Gaithersburg, Md.).

Peptide probe sequence I. Biotin-IEGRGS (KBv TAG Plus) amide (SEQ ID NO:6)

Peptide probe sequence II. Biotin-(mPeg2)IEGRGS (KBv TAG Plus) amide (SEQ ID NO:6)

mPeg2 is a hydrophilic 9-atom polyethylene spacer between the peptide cleavage sequence and a biotin molecule. The BV-TAG Plus is conjugated at the primary amine group on the side-chain of the lysine residue.

The preparation of biotin and BV-TAG Plus NHS Ester or BV TAG NHS ester conjugated peptides was contracted to New England Peptide LLC (65 Zub Lane, Gardner, Mass. 01440). The final products were purified by HPLC and verified with mass spectral analyses.

A FXa activity calibrator curve was set up in a 96-well U bottom microtiter plate containing a serial dilution of FXa in an assay buffer [20 mM Tris-HCl (pH 7.2), 100 mM NaCl, 0.5% BSA and 6.0 mM $CaCl_2$], with either peptide probe sequence I or II and M280-SA beads (Dynabeads M280-SA, Invitrogen, Cat: 112-06D). To each well was added 50 µL of 2-fold serial dilutions of FXa from 5000, 2500, 1250, 625, 313, 156 and 78.1 ng/mL and 50 µL of peptide probe (sequence I or II) at 10.0 ng/mL. The plate was incubated for 50 minutes on a MicroMix 5 shaker (Siemens) at room temperature and then 20 µL of 500 µg/mL M280-SA beads were added for an additional 10-minute incubation. The beads were washed once in 150 µL of a PBS-based buffer solution containing 1.8 mM $KH_2PO_4$, 10 mM $Na_2HPO_4$, 120 mM NaCl, 2.7 mM KCl, 0.033% Tween20 and 0.10% KATHON® CG/ICP II (Cat: 48178-U. Sigma, St. Louis, Mo.) and recovered by attaching a plate magnet to the 96-well plate (LIFESEP™ 96F, Dexter Magnetic Technologies Inc., Elk Grove Village, Ill. 60007). Beads were resuspended in 150 µL of the same PBS-based buffer and read in a M1MR Analyzer (Bioveris). The FXa activity was inversely correlated to the ECL signals as shown in Table 1. As can be seen from Table 1, the limit of detection for this particular assay was between 156-313 ng/mL after a total incubation of 60 minutes.

TABLE 1

| FXa Concentration (ng/mL) | Peptide Probe Sequence I | | Peptide Probe Sequence II | |
| --- | --- | --- | --- | --- |
| | Mean Signal | % Signal Decrease | Mean Signal | % Signal Decrease |
| 0 | 426545 | NA | 339346 | NA |
| 78.1 | 413958 | −3% | 339795 | 0% |
| 156 | 413232 | −3% | 325928 | −4% |
| 313 | 388137 | −9% | 302632 | −11% |
| 625 | 363185 | −15% | 305778 | −10% |
| 1250 | 296182 | −31% | 256745 | −24% |
| 2500 | 202007 | −53% | 208649 | −39% |
| 5000 | 103604 | −76% | 116839 | −66% |

Example 2

Preparation of BV TAG Plus-Conjugated ANTI-FLAG® M1 Antibody (at 15:1 Challenge Ratio)

5.0 mg ANTI-FLAG® M1 antibody (Cat: F3040-5MG. Sigma, St. Louis, Mo.) was buffer exchanged to a phosphate buffered saline containing 10.5 mM $KH_2PO_4$, 139.5 mM $K_2HPO_4$ and 150.6 mM NaCl, =pH 7.7-7.9 (typically pH 7.8.) in an AmiconUltra4-50K filter (Cat: UFC805024, Millipore, Billerica, Mass.). After the buffer exchange, the protein concentration of the antibody was measured by the BCA Protein Assay Reagents (Reagent A, Cat: 23223 and Reagent B, Cat: 23224, Thermo Fisher Scientific, Rockford, Ill.) against the Bovine Gamma Globulin Standard (Cat: 23213, Thermo Fisher Scientific, Rockford, Ill.). The protein concentration was 4.041 mg/mL and the total volume was approximately 1.0 mL.

To a 0.25 mL solution of ANTI-FLAG® M1 antibody (4.041 mg/mL) in a microcentrifuge tube, 20 µL of BV-TAG Plus NHS Ester (Cat: 23224, BioVeris, Gaithersburg, Md.) (5.0 nMole/µL) freshly prepared with ice-cold water (Milli Q Synthesis, Millipore, Billerica, Mass., 01821) was added and quickly mixed by tapping the tube. The solution was incubated and mixed continuously for 1 hour at room temperature. After the incubation, the antibody was buffer exchanged to phosphate buffered saline containing 37.5 mM $KH_2PO_4$, 112.5 mM $K_2HPO_4$, 150.6 mM NaCl and 0.10% 2-Methyl-4-isothiazolin-3-one Hydrochloride (MIT) and 7.0 mM $CaCl_2$. The post modification concentration was 0.852 mg/mL in approximately 1.0 mL.

Example 3

Preparation of Biotin-Conjugated ANTI-FLAG® M1 Antibody (10:1 Challenge Ratio)

The ANTI-FLAG® M1 antibody was buffer exchanged as in the Example 2.

An EZ-Link® Sulfo-NHS-LC Biotin stock (Cat: 23224, Thermo Fisher Scientific, Rockford, Ill.) was freshly prepared by adding 300 µL of ice-cold water in a single polypropylene microcentrifuge tube containing 1.0 mg of EZ-LINK® Sulfo-NHS-LC Biotin resulting in a concentration of 5.99 nMole/µL. To a 0.25 mL solution of ANTI-FLAG® M1 antibody (4.041 mg/mL) in a microcentrifuge tube, 11 µL of the freshly prepared EZ-LINK® Sulfo-NHS-LC Biotin water solution was added. This solution was incubated and mixed continuously for 1 hour at room temperature. After the incubation, the antibody was buffer exchanged to a phosphate buffered saline (PBS) containing 37.5 mM $KH_2PO_4$, 112.5 mM $K_2HPO_4$, 150.6 mM NaCl, 0.10% 2-Methyl-4-isothiazolin-3-one Hydrochloride (MIT), and 7 mM $CaCl_2$. The post modification concentration was 0.975 mg/mL in approximately 1.0 mL.

Example 4

Detecting FXa Activity by Detection of a Neoepitope with an Immunoassay Using a TAG Plus-Conjugated Detector Antibody FXa activity can be measured using peptides comprising a FXa recognition site (-IEGR-) (SEQ ID NO:1) at their N-terminus followed by an amino acid sequence which can be cleaved "off" by FXa. For example, peptide sequence III, below, can be cleaved by FXa to produce peptide sequence IV below. The FXa cleavage of the peptide bond after the arginine residue of the -IEGR- sequence (SEQ ID NO:1) produces a free $NH_2$ group at the N-terminal of the peptide sequence (sequence IV) and the peptide sequence becomes a new epitope (neoepitope) after cleavage.

```
Peptide sequence III.
                                          (SEQ ID NO: 5)
NH2-IEGRDYKDDDDKGS- Peptide sequence IV.
                                          (SEQ ID NO: 4)
NH2-DYKDDDDKGS- Peptide sequence V.
                                          (SEQ ID NO: 8)
Bz-IEGRDYKDDDDKGSHHHHHH(mPeg2)(KLCBiot)-amide
```

Peptides were synthesized by New England Peptide, LLC (Gardner, Mass.). KLCBiot is a biotin molecule conjugated to the amino group of the side chain of a lysine molecule.

A FXa activity calibrator curve was set up in a 96-well U bottom microtiter plate containing 100 µL of a 3-fold serial dilution of FXa at 500, 167, 55.6, 18.5, 6.17, 2.06 and 0.686 ng/mL in an assay buffer [50 mM Tris-HCl (pH 7.4), 100 mM NaCl, 0.5% BSA, 10 mg/mL ciprofloxacin, 0.5% Tween-20 and 7.0 mM CaCl$_2$] and 50 µL of a master mix of FXa detection reagent containing 200 µg/mL of M280-SA beads, 600 ng/mL of a peptide sequence V and 1000 ng/mL of TAG Plus anti-FLAG® M1 antibody (Example 2) in the same assay buffer. The peptide sequence V comprises peptide sequence III and a sequence HHHHHH(mPeg2)(KLCBiot)-amide (SEQ ID NO:9). The HHHHHH(mPeg2) (SEQ ID NO:9), a mini-PEG molecule with 9 carbon polyethylene molecule, serves as a spacer, which was conjugated with a lysine at its C-terminus. A biotin molecule was conjugated to the primary amine group on the side chain of the lysine. The peptide can be captured through the high affinity interaction between biotin and streptavidin molecule.

The plate was incubated on a hot plate (Digital Heatblock, Cat. 12621-100, VWR International, LLC., West Chester, Pa. 19380) at 37° C. for 10 or 20 minutes. After the incubation, the beads were washed once in 150 µL of the PBS-based buffer solution (Example 1) and recovered by attaching a plate magnet to the 96-well plate (LIFESEP™ 96F, Dexter Magnetic Technologies Inc., Elk Grove Village, Ill. 60007). Beads were resuspended in 150 µL of the PBS-based buffer and read in a M1MR analyzer. The FXa activity concentrations were correlated to the ECL signals as shown in Table 2. The 20 minute incubation produced significantly higher signal and signal/back than that of the 10 minute incubation. Under both incubation conditions, FXa activities were detectable at 1.00 ng/mL or lower concentrations of FXa (signal/background ≥3.0). This lower detection limit is unexpectedly much better than that achieved in Example 1.

TABLE 2

| FXa (ng/mL) | 10 minute incubation | | 20 minute incubation | |
|---|---|---|---|---|
| | Mean Signal | Signal/Background | Mean Signal | Signal/Background |
| 0.00 | 345 | NA | 319 | NA |
| 0.686 | 856 | 2.5 | 1047 | 3.3 |
| 2.06 | 1427 | 4.1 | 2109 | 6.6 |
| 6.17 | 3105 | 9.0 | 6035 | 19 |
| 18.5 | 8793 | 25 | 20653 | 65 |
| 55.6 | 33734 | 98 | 73974 | 232 |
| 167 | 113240 | 328 | 224915 | 706 |
| 500 | 298048 | 864 | 497703 | 1562 |

Example 5

Detecting FXa Activity by Detection of a Neoepitope Using a Competitive Assay Format Another method for detecting FXa activity uses a competitive immunoassay format. For example, peptide sequence VI, below, comprises a FXa recognition site (-IEGR-) (SEQ ID NO:1) at its N-terminus and the peptide sequence IV-amide (DYKDDDDKGS-amide) (SEQ ID NO:4) at its C-terminus. The FXa cleavage of the peptide bond after the arginine residue of -IEGR- (SEQ ID NO:1) sequence produces a neoepitope (SEQ ID NO:4), which can be measured with a TAG Plus-conjugated peptide (sequence VII) and a capture antibody in a competitive immunoassay format.

Peptide sequence VI.
(SEQ ID NO: 5)
NH$_2$-IEGRDYKDDDDKGS-amide

Peptide sequence VII.
(SEQ ID NO: 4)
NH$_2$-DYKDDDDKGS-TAG Plus

Peptides were synthesized by New England Peptide, LLC (Gardner, Mass.).

A FXa activity calibrator curve was set up in a 96-well U bottom microtiter plate containing 100 µL of a 3-fold serial dilution of FXa at 500, 167, 55.6, 18.5, 6.17, 2.06 and 0.686 ng/mL in the assay buffer (Example 4) and 50 µL of a master mix of FXa detection reagent containing 200 µg/mL of M280-SA beads prebound with biotinylated capture antibody (5.0 µg antibody per 1.0 mg of beads) (anti-FLAG® MD, 200 µg/mL of the NH$_2$-IEGRDYKDDDDKGS-amide (Peptide sequence VI; SEQ ID NO:5) and 100 ng/mL of NH$_2$-DYKD-DDDKGS-TAG Plus (Peptide sequence VII; SEQ ID NO:4) in the same assay buffer. The plate was incubated on a hot plate (Example 4) at 37° C. for 15 minutes. After the incubation, the beads were washed once in 150 µL of the PBS-based buffer solution (Example 3) and were resuspended in 150 µL of the PBS-based buffer and read in a M1MR analyzer (BioVeris). The FXa concentrations inversely correlated to the ECL signals as shown in Table 3. FXa activities were detectable at 1.0 ng/mL or lower concentrations which produced about a 10% decrease of the background signals (the sample without FXa).

TABLE 3

| Xa (ng/mL) | Mean Signal | % Signal Decrease |
|---|---|---|
| 0.00 | 91842 | NA |
| 0.686 | 84026 | −8.5% |
| 2.06 | 71945 | −22% |
| 6.17 | 52963 | −42% |
| 18.5 | 36383 | −60% |
| 55.6 | 22509 | −75% |
| 167 | 14300 | −84% |
| 500 | 9830 | −89% |

Example 6

Detecting FXa Activity by Detecting the Labeled Neoepitope Using a Capture Reagent A FXa activity calibrator curve was set up in a 96-well U bottom microtiter plate containing 50 µL of a 3-fold serial dilution of FXa at 1000, 333, 111, 37.0, 12.3, 4.12 and 1.37 ng/mL in the assay buffer (Example 4) and 25 µL of NH$_2$-IEGRDYKDDDDKGS-TAG (SEQ ID NO:5) (1.25, 2.5 or 5.0 µg/mL) in a hot plate at 37° C. for 10 minutes. After the incubation, 50 µL of Bi-anti-FLAG®-M1 antibody prebound beads (200 µg/mL concentration at the ratio of 10 µg of antibody per 1.0 mg of beads) were added, followed by an incubation for another 20 minutes at 37° C. After the incubation, the beads were washed once in 150 µL of the PBS-based buffer solution (Example 3) and were resuspended in 150 µL of the PBS-based buffer before beads were read in a M1MR analyzer (BioVeris). The FXa activity concentrations correlated to the ECL signals as shown in Table 4. FXa activities were detectable at FXa concentrations of 4.12 ng/mL or greater (signal/background ≥3.0).

TABLE 4

NH$_2$-IEGRDYKDDDDKGS-TAG (SEQ ID NO: 5)

| FXa (ng/mL) | 1.25 µg/mL | | 2.5 µg/mL | | 5.0 µg/mL | |
|---|---|---|---|---|---|---|
| | Mean Signal | Signal/ Background | Mean Signal | Signal/ Background | Mean Signal | Signal/ Background |
| 0.00 | 593 | NA | 856 | NA | 1768 | NA |
| 1.37 | 1140 | 1.9 | 1393 | 1.6 | 3725 | 2.1 |
| 4.12 | 2174 | 3.7 | 3828 | 4.5 | 6363 | 3.6 |
| 12.3 | 4437 | 7.5 | 7696 | 9.0 | 14866 | 8.4 |
| 37.0 | 10667 | 18 | 20144 | 24 | 32274 | 18 |
| 111 | 20521 | 35 | 41788 | 49 | 62147 | 35 |
| 333 | 52797 | 89 | 62747 | 73 | 78710 | 45 |
| 1000 | 69011 | 116 | 78193 | 91 | 86900 | 49 |

Example 7

Detecting FXa Activity with an Immunoassay that Uses a Single Epitope Sandwich Immunoassay (Metatype Binding Molecule)

A FXa activity calibrator curve is set up in a 96-well U bottom microtiter plate containing 50 µL of a 3-fold serial dilution of FXa at 1000, 333, 111, 37.0, 12.3, 4.12 and 1.37 ng/mL in the assay buffer (Example 4) and 25 µL of a master mix containing 1.0 mg/mL of NH$_2$-IEGRDYKDDDDKGS (SEQ ID NO:5), 200 µg/mL of Bi-anti-FLAG®-M1 antibody prebound beads and 2.0 µg/mL of a TAG Plus-conjugated detector antibody in a hot plate at 37° C. for 3 minutes. TAG Plus-conjugated detector antibody preferentially binds the complex comprised the neo-epitope (NH$_2$-DYKDDDDKGS) (SEQ ID NO:4) captured on the Bi-anti-FLAG®-M1. After the incubation, the beads are washed once in 150 µL of the PBS-based buffer solution (Example 3) and are resuspended in 150 µL of the PBS-based buffer before beads are read in a M1MR Analyzer (Bioveris). The FXa activity concentrations positively correlate to the ECL signals.

One expected advantage of this format is high concentrations of substrate can be used that will shorten the required incubation time, thereby shortening the total length of time for the assay to be performed and improving the assay sensitivity.

Example 8

Detecting Plasma FVIII Activity by Detecting FXa Activity Using an Immunoassay

A FVIII activity calibrator curve was set up in a 96-well U bottom microtiter plate, which was equilibrated to 37° C. in an incubator. To 50 µL of a factor reagent containing 0.15 µM bovine FIXa (Cat: BCIX-A-1050, Haematologic Technologies, Inc. (HTI) Essex Junction, Vt. 05452), 0.12 µM bovine α-thrombin (Cat: BCT-1020, HTI), 0.40 µM bovine FX (Cat: BCX-1050, HTI), 45 µM phosphorliposome (80% phosphatidylcholine (Cat: 840051C) and 20% phosphatidylserine (Cat: 840032C, Avanti Polar Lipids, Inc. Alabaster, Ala.)), and 1.5 mM Gly-Pro-Arg-Pro amide (Cat: GPRP-NH$_2$, Sigma, St. Louis; SEQ ID NO:32) 25 µL of a diluted reference plasma (HEMOSIL™ Calibration Plasma, Cat: 0020003700, Diapharma Group Inc., Columbus, Ohio) containing 21.8, 7.27, 2.42, 0.807, 0.269, 0.0897 and 0.0299 mU/mL of FVIII in the assay buffer (Example 4) was added, mixed and incubated for exactly 5 minutes in a hot plate set at 37° C. After the incubation, to the 75 µL of assay mixture, 25 µL of 25 mM CaCl$_2$ was added and incubated for 10 minutes at 37° C. Then to the 100 µL of assay mixture, 50 µL of a master mix of FXa detection reagent, containing 200 µg/mL of M280-SA beads, 600 ng/mL of a peptide (peptide sequence V), 1000 ng/mL of TAG Plus anti-FLAG® M1 antibody (Example 2) and 30 µg/mL I-2581 (synthetic thrombin inhibitor, cat: 82110810. DiaPharma Columbus, Ohio) in the assay buffer (Example 4), were added and incubated for a final 30 minutes at 37° C. After the incubation, the beads were washed once in 150 µL of the PBS-based buffer solution (Example 3) and were resuspended in 150 µL of the PBS-based buffer before beads were read in a M1MR Analyzer (BioVeris). The FVIII activity concentrations were correlated to the ECL signals as shown in Table 5.

TABLE 5

| FVIII (mU/mL) | Mean Signal | Signal/Background |
|---|---|---|
| 0.000 | 17504 | NA |
| 0.0299 | 19386 | 1.1 |
| 0.0897 | 19514 | 1.1 |
| 0.269 | 21681 | 1.2 |
| 0.807 | 26983 | 1.5 |
| 2.42 | 44154 | 2.5 |
| 7.27 | 106424 | 6.1 |
| 21.8 | 168336 | 9.6 |

Example 9

Detecting Plasma FIX Activity by Detecting FXa Activity Using an Immunoassay

A FIX activity calibrator curve was set up in a 96-well U bottom microtiter plate, which was equilibrated to 37° C. in an incubator. All coagulating factor reagents were from Haematologic Technologies, Inc. ((HTI), Essex Junction, Vt.), unless specifically noted. To 50 μL of a factor reagent containing 1.6 nM bovine FXIa (Cat: HCX1A-0160), 0.0681 nM bovine α-thrombin (Cat: BCT-1020), 24.5 nM bovine FX (BCX-1050), 0.152 nU/mL FVIII (Cat: PRO-318, PROSPEC, Rehovot, Israel), 100 μM phosphorliposome (80% phosphatidylcholine and 20% phosphatidylserine) and 0.75 mM Gly-Pro-Arg-Pro amide (Cat: GPRP-NH$_2$. Sigma, St. Louis; SEQ ID NO:32), 25 μL of a diluted reference plasma (HEMOSIL™ Calibration Plasma, Cat: 0020003700, Diapharma Group Inc., Columbus, Ohio) containing 24.4, 8.13, 2.71, 0.904, 0.301, 0.100 and 0.0335 mU/mL of FIX in the assay buffer (Example 4) were added, mixed and incubated for exactly 10 minutes in a hot plate set at 37° C. After the incubation, to the 75 μL of assay mixture, 50 μL of a master mix of FXa detection reagent (Example 4), containing 200 μg/mL of M280-SA beads, 600 ng/mL of a peptide (peptide sequence III), 1000 ng/mL of TAG Plus anti-FLAG® M1 antibody (Example 2), and 30 μg/mL I-2581 (synthetic thrombin inhibitor, cat: 82110810, DiaPharma Group Inc. West Chester, Ohio 45069) in assay buffer (Example 4) was added and incubated for a final 20 minutes at 37° C. After the incubation, the beads were washed once in 150 μL of a PBS-based buffer solution (Example 3) and were resuspended in 150 μL of the same buffer before beads were read in a M1MR analyzer (BioVeris). The FIX activity concentrations correlated to the ECL signals as shown in Table 6.

TABLE 6

| FIX (mU/mL) | Mean Signal | Signal/Background |
|---|---|---|
| 0.000 | 3444 | NA |
| 0.0335 | 3665 | 1.1 |
| 0.100 | 4050 | 1.2 |
| 0.301 | 5626 | 1.6 |
| 0.904 | 8707 | 2.5 |
| 2.71 | 16884 | 4.9 |
| 8.13 | 30879 | 9.0 |
| 24.4 | 40234 | 11.7 |

Example 10

Detecting Heparin Activity with an ECL-Based FXa Activity Immunoassay

A heparin activity calibrator curve was set up in a 96-well U bottom microtiter plate, which was equilibrated to 37° C. in an incubator. To each well, 25 μL of 100, 50, 25, 12.5, 6.25 and 3.13 mIU/mL heparin prepared from a heparin sodium Salt (Cat: H4784-2500MG, Sigma, St. Louis) and 25 μL of 1.0 IU/mL human antithrombin (from kit of BIOPHEN Heparin Anti-Xa, Ref: 221010, Aniara Diagnostica LLC, Columbus, Ohio) were added and incubated for 2 minutes at 37° C. Then to the mixture, 25 μL of 8.0 μg/mL bovine factor Xa (from kit of BIOPHEN Heparin Anti-Xa, Ref: 221010, Aniara Diagnostica LLC, Columbus, Ohio) was added, followed immediately with 25 μL of a master mix of FXa detection reagent containing 400 μg/mL of M280-SA beads, 1.2 μg/mL of a peptide (peptide sequence V), 2.0 μg/mL of TAG Plus anti-FLAG® M1 antibody (Example 2) and 25 mM CaCl$_2$. The subsequent mixture was incubated for a final 20 minutes at 37° C. After the incubation, the beads were washed once in 150 μL of the PBS-based buffer solution (Example 3) and were resuspended in 150 μL of the same buffer before beads were read in a M1MR Analyzer (BioVeris). The heparin activity was correlated to the ECL signals as shown in Table 7.

TABLE 7

| Heparin (mIU/mL) | Mean Signal | % Signal Decrease |
|---|---|---|
| 0.00 | 101221 | NA |
| 3.13 | 81999 | −19% |
| 6.25 | 62502 | −38% |
| 12.5 | 40868 | −60% |
| 25.0 | 19648 | −81% |
| 50.0 | 7203 | −93% |
| 100 | 3322 | −97% |

Example 11

Detecting Plasma FVII Activity with an ECL-Based FXa Activity Immunoassay

FVII is the serine esterase of the extrinsic coagulation pathway. When complexed to Tissue Factor (TF), in the presence of phospholipids and calcium, FVII activates FX to FXa. Factor VII forms an enzymatic complex with TF (e.g., provided by rabbit thromboplastin). It can then activate FX that is present in the assay. Factor Xa then can cleave the peptide substrate (e.g., peptide sequence V). The amount of cleaved substrate can be detected by detecting a neo-binding-site such as SEQ ID NO:2, e.g., as described herein. The amount of cleaved substrate is directly proportional to the FXa activity, which has a direct relationship to the amount of Factor VII in the assayed sample. In some embodiments, the Factor VII activity can be determined in an ECL analyzer.

All publications, patents and patent applications mentioned in this specification are herein incorporated by reference in their entirety into the specification to the same extent as if each individual publication, patent or patent application was specifically and individually indicated to be incorporated herein by reference.

The invention claimed is:

1. A method of detecting protease activity in a sample, comprising:

combining in a solution at least the sample and a substrate under conditions compatible for the protease activity, wherein the substrate comprises an amino acid sequence selected from the group consisting of IEGRDYKD-DDDKGSHHHHHH (SEQ ID NO:8), IDGRDYKD-DDDK (SEQ ID NO:41), IDGRDYKDDDDKGS (SEQ ID NO:42), IDGRDYKDDDDKGSHHHHHH (SEQ ID NO:43), AEGRDYKDDDDK (SEQ ID NO:44), AEGRDYKDDDDKGS (SEQ ID NO:45), and AEGRDYKDDDDKGSHHHHHH (SEQ ID NO:46), wherein the amino acid sequence comprises a cleavage site for the protease, wherein cleavage at the cleavage site generates a neo-binding-site, and wherein the cleavage site is heterologous with respect to the neo-binding-site;

previously, subsequently or concurrently adding to the solution a first binding molecule, wherein the first binding molecule preferentially binds the neo-binding-site after cleavage of the substrate by the protease activity as compared to binding to the neo-binding-site in the uncleaved substrate; and detecting the binding of the first binding molecule to a fragment of the cleaved substrate.

2. The method of claim 1, wherein the protease activity is factor Xa (FXa) activity.

3. The method of claim 2, wherein the cleavage site comprises an amino acid sequence selected from the group consisting of IEGR (SEQ ID NO:1), IDGR (SEQ ID NO:39), and AEGR (SEQ ID NO:40).

4. The method of claim 1, wherein the neo-binding-site is located or bound to the uncleaved substrate at a site carboxy-terminal to the cleavage site.

5. The method of claim 1, method of claim 1, wherein the cleavage site comprises an amino acid sequence selected from the group consisting of IEGR (SEQ ID NO:1), IDGR (SEQ ID NO:39), AEGR (SEQ ID NO:40), DEVD (SEQ ID NO:13), IETD (SEQ ID NO:14), VDVAD (SEQ ID NO:15), VEID (SEQ ID NO:16), YVAD (SEQ ID NO:17), DALD (SEQ ID NO:18), VEVD (SEQ ID NO:19), VEMD (SEQ ID NO:20), SSTD (SEQ ID NO:21) and WEND (SEQ ID NO:22).

6. The method of claim 1, wherein the solution comprises GPRP-NH2 (SEQ ID NO:32).

7. The method of claim 1, wherein the solution comprises calcium.

8. The method of claim 1, wherein the solution comprises a blocker of fibrin network formation.

9. The method of claim 2, wherein the method is used to quantify the amount of the factor Xa activity in the sample.

10. The method of claim 1, wherein the substrate comprises an amino acid sequence selected from the group consisting of SEQ ID NO:2 and SEQ ID NO:4.

11. The method of claim 10, wherein amino acid sequence SEQ ID NO:2 or SEQ ID NO:4 is immediately carboxy-terminal to the FXa cleavage site.

12. The method of claim 1, wherein the substrate is bound to a surface and the surface binds the substrate at a site carboxy-terminal of the cleavage site.

13. The method of claim 1, wherein the neo-binding-site comprises an amino acid sequence.

14. The method of claim 13, wherein the neo-binding-site comprises an amino acid sequence selected from the group consisting of DYKDDDDK (SEQ ID NO:2), DIP EN (SEQ ID NO:33), ARG (SEQ ID NO:34), ARGSV (SEQ ID NO:35), ARGSVIL (SEQ ID NO:36) and FFGV (SEQ ID NO:37).

15. The method of claim 1, wherein the first binding molecule is selected from the group consisting of an antibody, an aptamer, a ligand and a receptor.

16. The method of claim 1, wherein the first binding molecule comprises at least one detection label.

17. The method of claim 16, wherein the at least one detection label is selected from an electrochemiluminescence label, an enzyme label, a fluorophore, a latex particle, a magnetic particle, a radioactive element, a phosphorescent dye, a dye crystalite, a gold particle, a silver colloidal particle, a selenium colloidal particle, a metal chelate, a coenzyme, an electro active group, an oligonucleotide and a stable radical.

18. The method of claim 17, wherein the metal chelate is a ruthenium or an osmium metal chelate.

19. A method of detecting protease activity in a sample, comprising:
  combining in a solution at least the sample and a substrate under conditions compatible for the protease activity,
  wherein the substrate comprises an amino acid sequence consisting of the sequence set forth in IEGRDYKDDDDK (SEQ ID NO:3) or IEGRDYKDDDDKGS (SEQ ID NO:5),
  wherein the amino acid sequence comprises a cleavage site for the protease,
  wherein cleavage at the cleavage site generates a neo-binding-site, and
  wherein the cleavage site is heterologous with respect to the neo-binding-site;
  previously, subsequently or concurrently adding to the solution a first binding molecule, wherein the first binding molecule preferentially binds the neo-binding-site after cleavage of the substrate by the protease activity as compared to binding to the neo-binding-site in the uncleaved substrate; and
  detecting the binding of the first binding molecule to a fragment of the cleaved substrate.

20. The method of claim 19, wherein the protease activity is factor Xa (FXa) activity.

21. The method of claim 20, wherein the cleavage site comprises an amino acid sequence selected from the group consisting of IEGR (SEQ ID NO:1), IDGR (SEQ ID NO:39), and AEGR (SEQ ID NO:40).

22. The method of claim 19, wherein the solution comprises a blocker of fibrin network formation.

23. The method of claim 22, wherein the method is used to quantify the amount of the factor Xa activity in the sample.

24. The method of claim 19, wherein the substrate comprises an amino acid sequence selected from the group consisting of SEQ ID NO:2 and SEQ ID NO:4.

25. The method of claim 24, wherein amino acid sequence SEQ ID NO:2 or SEQ ID NO:4 is immediately carboxy-terminal to the FXa cleavage site.

26. The method of claim 19, wherein the substrate is bound to a surface and the surface binds the substrate at a site carboxy-terminal of the cleavage site.

27. The method of claim 19, wherein the neo-binding-site comprises an amino acid sequence.

28. The method of claim 27, wherein the neo-binding-site comprises an amino acid sequence selected from the group consisting of DYKDDDDK (SEQ ID NO:2), DIP EN (SEQ ID NO:33), ARG (SEQ ID NO:34), ARGSV (SEQ ID NO:35), ARGSVIL (SEQ ID NO:36) and FFGV (SEQ ID NO:37).

29. The method of claim 19, wherein the first binding molecule is selected from the group consisting of an antibody, an aptamer, a ligand and a receptor.

30. The method of claim 19, wherein the first binding molecule comprises at least one detection label.

31. The method of claim 30, wherein the at least one detection label is selected from an electrochemiluminescence label, an enzyme label, a fluorophore, a latex particle, a magnetic particle, a radioactive element, a phosphorescent dye, a dye crystalite, a gold particle, a silver colloidal particle, a selenium colloidal particle, a metal chelate, a coenzyme, an electro active group, an oligonucleotide and a stable radical.

32. The method of claim 31, wherein the metal chelate is a ruthenium or an osmium metal chelate.

* * * * *